US012752127B2

(12) United States Patent
Le et al.

(10) Patent No.: US 12,752,127 B2
(45) Date of Patent: Oct. 6, 2026

(54) TEST DEVICE, METHOD, AND SYSTEM FOR TREATING ALZHEIMER'S DISEASE

(71) Applicant: The First Affiliated Hospital of Dalian Medical University, Dalian (CN)

(72) Inventors: Weidong Le, Dalian (CN); Song Li, Dalian (CN); Jun Zhang, Dalian (CN); Congcong Jia, Dalian (CN); Yixin Chen, Dalian (CN); Hongbin Ding, Dalian (CN); Yarui Zhao, Dalian (CN)

( * ) Notice: Subject to any disclaimer, the term of this patent is extended or adjusted under 35 U.S.C. 154(b) by 252 days.

(21) Appl. No.: 18/436,095

(22) Filed: Feb. 8, 2024

(65) Prior Publication Data

US 2025/0256123 A1 Aug. 14, 2025

(51) Int. Cl.

| | |
|---|---|
| ***A61N 5/06*** | (2006.01) |
| ***A61B 5/00*** | (2006.01) |
| ***A61M 16/06*** | (2006.01) |

(52) U.S. Cl.

CPC .......... *A61N 5/0622* (2013.01); *A61B 5/4088* (2013.01); *A61B 5/4836* (2013.01); *A61M 16/06* (2013.01); *A61B 2503/40* (2013.01); *A61B 2503/42* (2013.01); *A61N 2005/0626* (2013.01); *A61N 2005/0647* (2013.01)

(58) Field of Classification Search

CPC .......... A61N 5/0622; A61N 2005/0647; A61B 5/4088; A61B 5/4836; A61D 3/00; A61M 16/06

See application file for complete search history.

(56) References Cited

U.S. PATENT DOCUMENTS

| | | | | |
|---|---|---|---|---|
| 6,469,498 B1 * | 10/2002 | Steinich | G01B 7/003 | 324/207.13 |
| 2004/0082984 A1 * | 4/2004 | Osorio | A61B 5/4094 | 607/116 |
| 2007/0055289 A1 * | 3/2007 | Scouten | A61B 90/14 | 606/130 |
| 2009/0254154 A1 * | 10/2009 | De Taboada | A61N 5/0613 | 607/110 |
| 2013/0042332 A1 * | 2/2013 | Chen | A61B 5/1036 | 800/9 |
| 2016/0235983 A1 * | 8/2016 | Berman | A61N 2/006 | |
| 2017/0035982 A1 * | 2/2017 | Roseman | A61B 5/055 | |

OTHER PUBLICATIONS

Long Niu, et al., Chronic sleep deprivation altered the expression of circadian clock genes and aggravated Alzheimer's disease neuropathology, Brain Pathology, 2022, pp. 1-15, vol. 32.

(Continued)

*Primary Examiner* — Alireza Nia

(57) ABSTRACT

A test device, a test method, and a test system for treating AD are provided. The test device for AD includes: a THz wave generator, used for generating THz wave; a headgear, connected to the THz wave generator via an optical fiber, is utilized for precise irradiation of the THz wave to a specific brain region in the experimental animals. The test device solves the defect that there is still no effective treatment for cognitive dysfunction diseases such as AD and VD, and it can provide a new idea for the treatment of AD through the THz irradiation test.

10 Claims, 35 Drawing Sheets

(56) References Cited

OTHER PUBLICATIONS

Ying Wang, et al., The essential role of transcription factor Pitx3 in preventing mesodiencephalic dopaminergic neurodegeneration and maintaining neuronal subtype identities during aging, Cell Death and Disease, 2021, pp. 1-11, 12:1008.
John Hardy, et al., The Amyloid Hypothesis of Alzheimer's Disease: Progress and Problems on the Road to Therapeutics, Science, 2002, pp. 353-356, vol. 297.
K. Blennow, et al., Biomarkers for Alzheimer's disease: current status and prospects for the future, J Intern Med, 2018, pp. 643-663, vol. 284.
Takayasu Kawasaki, et al., Infrared Laser Induced Amyloid Fibril Dissociation: A Joint Experimental/Theoretical Study on the GNNQQNY Peptide, The Journal of Physical Chemistry, 2020, pp. 1-38.
Guozhi Liu, The conjectures on physical mechanism of vertebrate nervous system, Science China Press, 2018, pp. 3864-3865, vol. 63, No. 36.

* cited by examiner

TEST DEVICE, METHOD, AND SYSTEM FOR TREATING ALZHEIMER'S DISEASE

TECHNICAL FIELD

The present disclosure relates to the technical field of biomedicine, in particular to a test device, a test method, and a test system for treating Alzheimer's disease (AD).

BACKGROUND

Terahertz (THz) waves range between microwave and infrared regions in the electromagnetic spectrum. Electromagnetic stimulation technology has been considered a novel non-invasive method for AD because of its great therapeutic potential, light side effects, and easy acceptance. The vibrational and rotational energy levels of numerous biomacromolecules situate within the THz frequency range. Existing research demonstrates that brain electromagnetic stimulation can induce long-term effects on neurotransmitter metabolism and synaptic plasticity by modulating the excitability of the cerebral cortex, and can ameliorate cognitive function. In 2018, Liu speculated that the physical field of biological nerve signals could potentially manifest as a high-frequency electromagnetic field ranging from THz to infrared. The THz fields have been demonstrated to exert control over various physiological processes, including the unwinding of DNA hairpins and the activation of ion channels. The mechanism is that THz wave resonates with biomacromolecules and modifies the hydrogen bonds (H-bonds) formed in them. Furthermore, it has been reported that the intermolecular hydrogen bonding network plays a vital role in modulating the formation of amyloid fibrils. Kawasaki et al. found that THz irradiation can dissociate amyloid fibrils. Drawing inspiration from these findings, the utilization of resonance characteristics for the regulation of amyloid fibrils and prevention of undesired protein aggregation holds significant promise in ameliorating AD pathology. The abnormal accumulation and deposition of β-amyloid (Aβ) in the brain is the driving factor of AD, and it also serves important pathological bases. Senile plaques (SPs) formed by the deposition of Aβ in brain can induce a series of pathological changes such as hyperphosphorylation of tau protein, neuronal loss and synaptic degeneration. Therefore, targeted reduction of Aβ accumulation represents a promising strategy for attenuating or preventing the progression of AD. Currently, there remains a dearth of effective treatments for cognitive dysfunction diseases such as AD and vascular dementia (VD), thereby necessitating the exploration of novel therapies.

SUMMARY

The present disclosure provides a test device, a test method, and a test system for the treatment of AD. These advancements aim to address the current lack of effective treatment methods for cognitive dysfunction diseases such as AD and VD, while also offering a novel approach utilizing THz irradiation for the treatment of AD.

The present disclosure provides a test device for treating AD, comprising:

a THz wave generator, used for generating THz wave;

a headgear, connected to the THz wave generator via an optical fiber, is utilized for precise irradiation of the THz wave to a specific brain region in experimental animals.

The test device for treating AD according to the present disclosure, wherein further comprises:

a gas anesthesia machine and an anesthetic nasal mask, wherein the gas anesthesia machine continuously administers isoflurane to anesthetize the experimental animals, while the anesthetic nasal mask is positioned on their noses for the delivery of isoflurane.

The test device for treating AD according to the present disclosure, wherein the THz wave generator comprises a THz wave irradiation output, a direction indicator, a ventilation system, a power connector, an overheating LED, a modulation input, and a power switch.

The test device for treating AD according to the present disclosure, wherein an inner side of the headgear is provided with an irradiation probe, the irradiation probe comprises a THz irradiation probe.

The test device for treating AD according to the present disclosure, wherein an outer side of the headgear is provided with a connecting hole, the position of the connecting hole corresponds to the position of the irradiation probe, and the headgear is connected with the THz wave generator through the connecting hole.

The test device for treating AD according to the present disclosure, wherein further comprises a pulse regulator;

the pulse regulator is connected to the THz wave generator via a coaxial transmission line, and the pulse regulator is used for modulating the pulse intensity of the THz wave emitted by the THz wave generator.

The test device for treating AD according to the present disclosure, wherein further comprises a stereotaxic apparatus;

the stereotaxic apparatus, used for fixing and adjusting the position of the experimental animals, ensuring accurate irradiation of the specific brain region by the THz wave emitted from the THz wave generator.

The disclosure also provides a test method for treating AD, comprising:

anesthetizing experimental animals and fixing them in a stereotaxic apparatus;

irradiating the experimental animals with THz wave to obtain irradiated experimental animals, wherein an irradiation power of the THz wave is 25 $mW/cm^2$;

conducting behavioral and pathological tests on the irradiated experimental animals, and determining a treatment result.

The present disclosure also provides a test system for treating AD, comprising:

an anesthesia module, used for anesthetizing experimental animals and fixing them in a stereotaxic apparatus;

an irradiation module, used for irradiating the experimental animals with THz wave, wherein an irradiation power of the THz wave is 25 $mW/cm^2$;

a detection module, used for conducting behavioral and pathological tests on the experimental animals exposed to THz wave, thereby determining a treatment outcome.

The present disclosure also provides an electronic device, comprising memory, a processor, and a computer program stored in the memory and executable on the processor, wherein when the processor executes the computer program, any one of the above-mentioned test methods for AD is realized.

The present disclosure also provides a non-transient computer-readable storage medium, on which a computer program is stored, which, when executed by a processor, realizes any one of the above-mentioned test methods for AD.

The present disclosure also provides a computer program product, comprising a computer program, which, when executed by a processor, realizes any of the above-mentioned test methods for treating AD.

The present disclosure discloses a device and a method for enhancing the cognitive function of AD through THz irradiation. This includes a THz irradiation platform for experimental animals, monitoring body temperature during the irradiation process, and an evaluation system to assess the effects of THz irradiation. These devices enable non-invasive physical intervention therapy using THz irradiation. The embodiments demonstrate that this device effectively improves the cognitive function of AD, offering new insights for future clinical treatment and research in this field.

BRIEF DESCRIPTION OF THE DRAWINGS

To describe the technical schemes in the embodiments of the present disclosure or in the prior more clearly, the following section will briefly introduce the drawings required to be used in the description of the examples. It is evident that the drawings in the following description are only examples of the present disclosure, and those ordinary skilled in the art may still obtain other drawings based on the provided drawings without creative work.

Among them:

1—THz wave generator; 2—pulse regulator; 3—coaxial transmission line; 4—horn antenna; 5—lens; 6—optical fiber; 7—headgear; 8—infrared thermal imager; 9—stereotaxic apparatus; 10—gas anesthesia machine; 11—connecting pipe; 12—anesthetic nasal mask; 13—irradiation site of left skull; 14—irradiation site of right skull; 201—THz wave irradiation output; 202—direction indicator; 203—ventilation system; 204—power connector; 205—overheating LED; 206—modulation input; 207—power switch.

DETAILED DESCRIPTION OF THE EMBODIMENTS

The technical solutions in the examples of the present disclosure will be clearly and completely described below about drawings in the examples. The described examples are only a part of examples and not all of them. Based on the examples of the present disclosure, all other examples obtained by those ordinary skilled in the art without creative work shall fall within the protection scope of the present disclosure.

Figure 1:
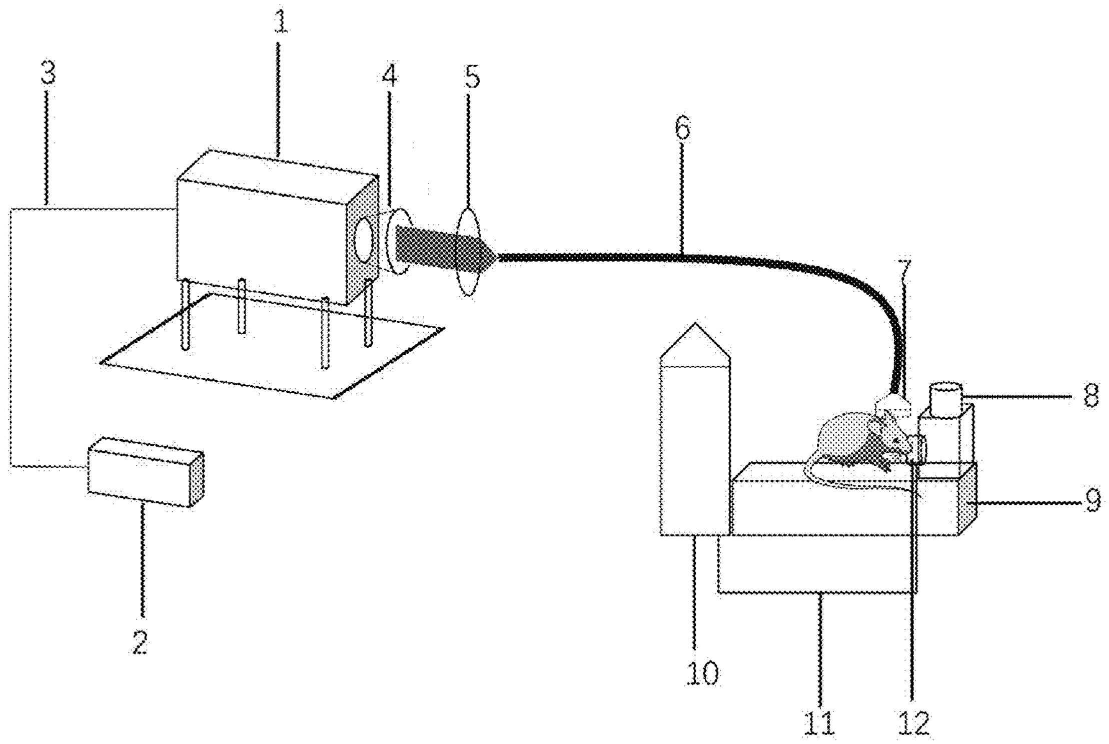
FIG. 1 is a schematic structural diagram of a test device for treating AD provided by an embodiment of the present disclosure.

FIG. 1 is a schematic structural diagram of a test device for treating AD provided by an embodiment of the present disclosure;

As shown in FIG. 1, the present disclosure also provides a test device for treating AD, comprising:

THz wave generator 1, pulse regulator 2, coaxial transmission line 3, horn antenna 4, lens 5, optical fiber 6, headgear 7, infrared thermal imager 8, stereotaxic apparatus 9, gas anesthesia machine 10, connecting pipe 11 and anesthetic nasal mask 12.

The THz wave generator 1 is used for generating low-frequency THz wave;

A signal output port of the pulse regulator 2 is connected with a signal input port of the THz wave generator 1 through a coaxial transmission line 3;

A horn antenna 4 is used for converging THz wave;

A lens 5 is used for focusing THz wave;

An optical fiber 6 may efficiently transmit THz wave;

A headgear 7 is used for connecting with the end of the optical fiber 6, an inner side of the headgear 7 is provided with an irradiation probe, and the irradiation probe comprises a THz irradiation probe, wherein the THz irradiation probe is used for emitting THz wave;

The localization of THz irradiation on the brain region is 2.0 mm anteroposterior, ±1.4 mm mediolateral, and 1.5 mm dorsoventral from bregma;

The irradiation site of THz wave on the brain region comprises the left skull 13 and the right skull 14;

An infrared thermal imager 8 is used for monitoring the temperature of experimental animals;

The stereotaxic apparatus 9 is used for accurately adjusting to the designated brain region for THz irradiation;

A gas anesthesia machine 10 is used to administer isoflurane for the anesthesia of mice;

A connecting pipe 11 is used for connecting the gas anesthesia machine 10 and the anesthetic nasal mask 12;

An anesthetic nasal mask 12 is covered on the nose of the experimental animal.

When in use, THz wave is firstly transmitted through the optical fiber 6, the diameter of which is 2.8 mm, and the end of the optical fiber is connected with the headgear 7 for fixing the head of the experimental animal, which directly acts on the specific brain region of the experimental animal; secondly, the gas anesthesia machine 10 is connected with the anesthetic nasal mask 12 through the connecting pipe 11, and the anesthetic nasal mask 12 is covered on the nose of the mouse, and the anesthetized mouse is fixed on the stereotaxic apparatus 9, and is accurately adjusted to the brain region to be irradiated; finally, a fixing headgear is put on the head of the experimental animal to ensure the effectiveness of THz irradiation.

Figure 2A:
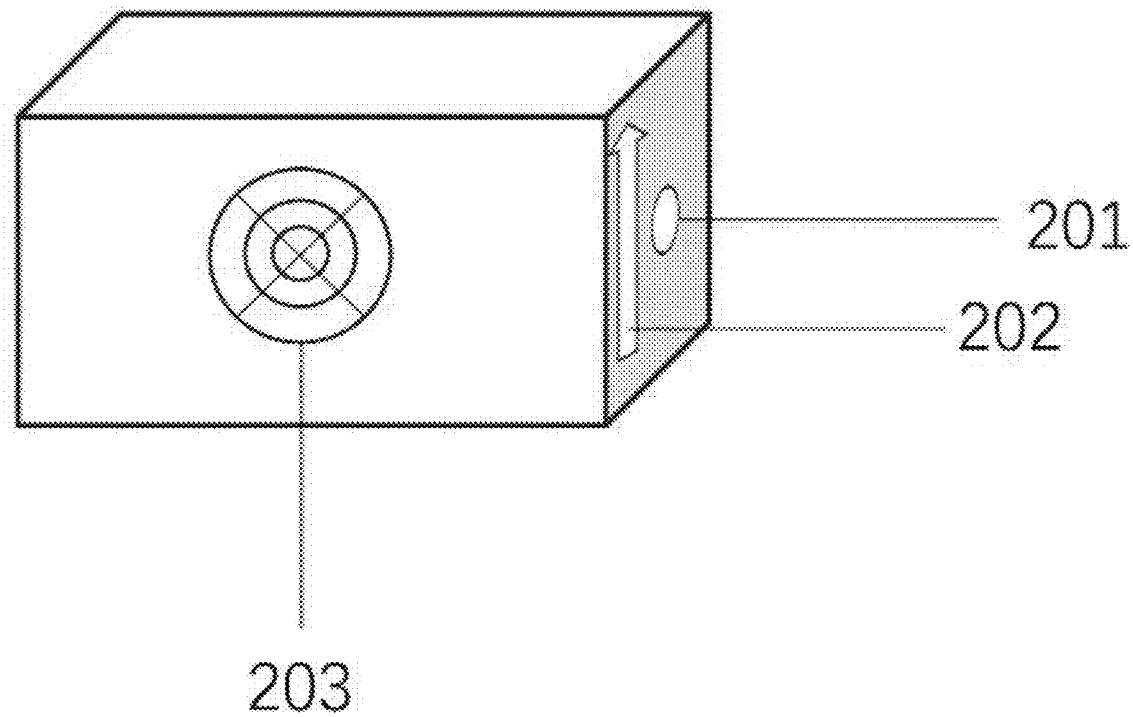
FIGS. 2A-2B are schematic structural diagrams of the THz wave generator provided by an embodiment of the present disclosure.
Figure 2B:
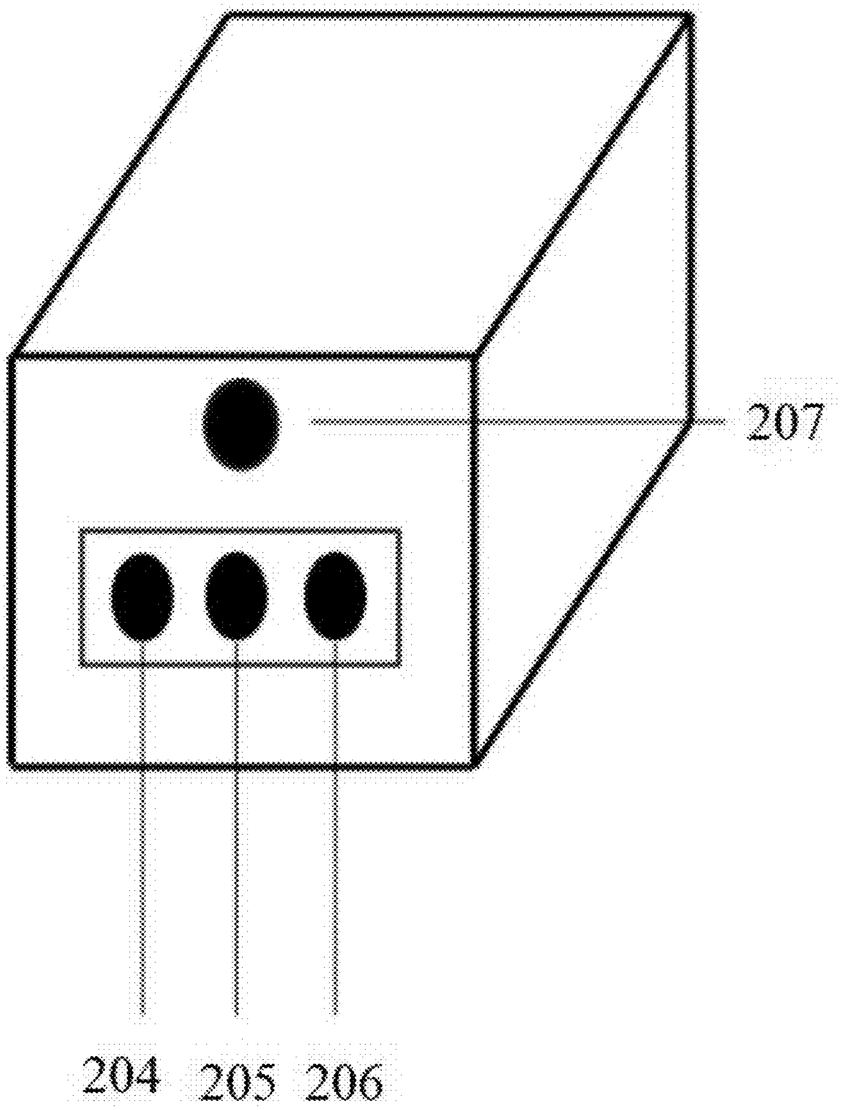

FIGS. 2A-2B are schematic structural diagrams of the THz wave generator provided by an embodiment of the present disclosure; the structure of the THz wave generator provided by this embodiment comprises a THz wave irradiation output 201, a direction indicator 202, a ventilation system 203, a power connector 204, an overheating LED 205, a modulation input 206, and a power switch 207.

Figure 3:
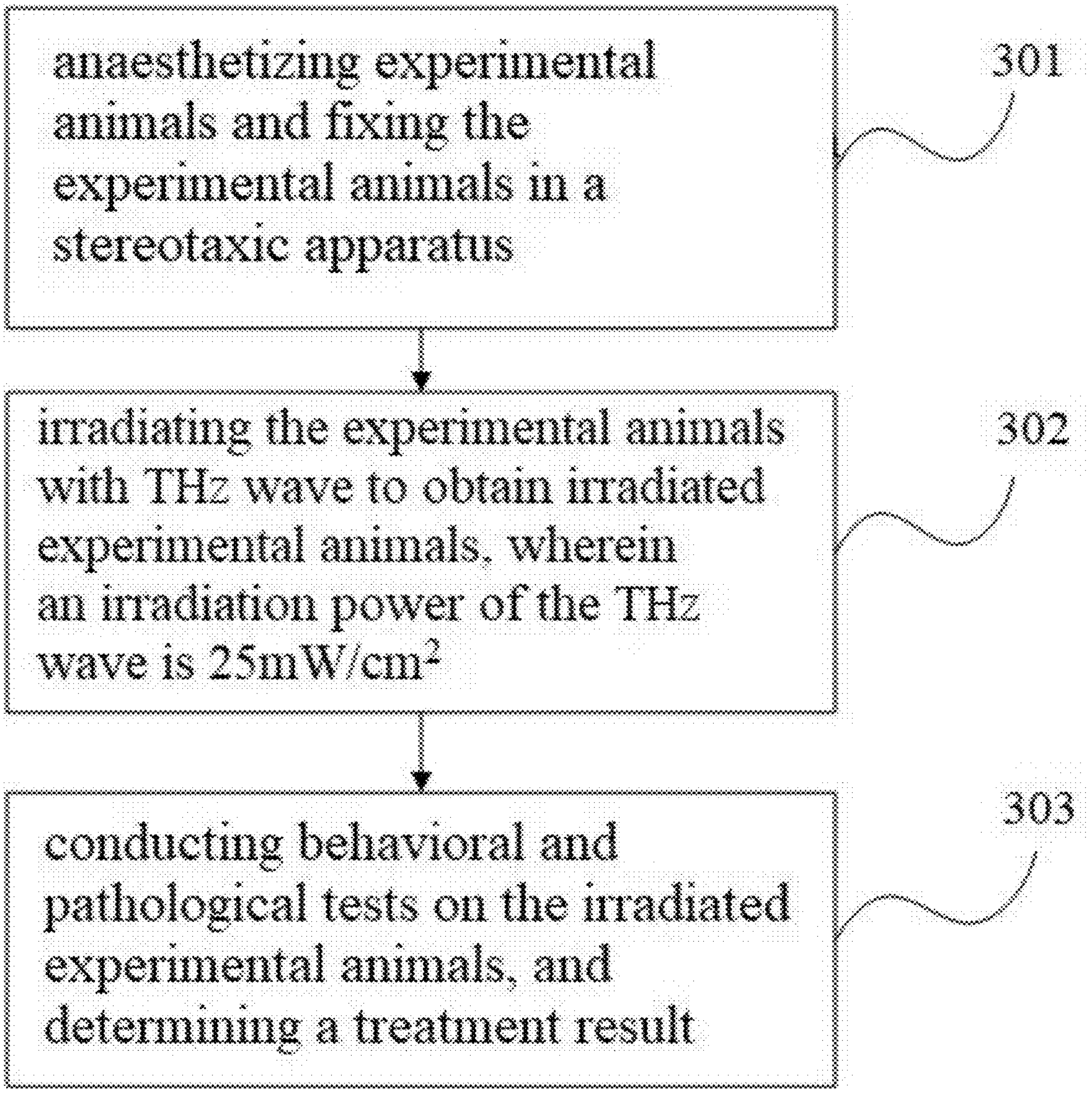
FIG. 3 is a flow chart of a test method for treating AD provided by an embodiment of the present disclosure.

FIG. 3 is a flow chart of the test method for treating AD provided by an embodiment of the present disclosure.

As shown in FIG. 3, the embodiment provides a test method for treating AD, comprising:

Step 301, anesthetizing experimental animals and fixing the experimental animals in a stereotaxic apparatus;

Step 302, irradiating the experimental animals with THz wave to obtain irradiated experimental animals, wherein an irradiation power of the THz wave is 25 $mW/cm^2$;

Step 303, conducting behavioral and pathological tests on the irradiated experimental animals, and determine a treatment result.

In an exemplary embodiment, the experimental animals are subjected to continuous anesthesia with isoflurane.

In an exemplary embodiment, irradiating the experimental animals with THz wave comprises:

irradiating the bilateral cortex and hippocampus area of the experimental animals with THz wave.

In an exemplary embodiment, irradiating the experimental animals with THz wave comprises:

irradiating the brain region (2.0 mm anteroposterior, ±1.4 mm mediolateral, and 1.5 mm dorsoventral from bregma) of the experimental animal with THz wave.

In an exemplary embodiment, further comprising: monitoring the body temperature of the experimental animals during THz irradiation and triggering an alarm if there is a deviation beyond a predetermined range.

In an exemplary embodiment, the predetermined range is ±0.1 degree centigrade.

Hereinafter, the test system for AD provided by the present disclosure will be described, and the test system for AD described below and the test method for treating AD described above can be referenced correspondingly.

Figure 4:
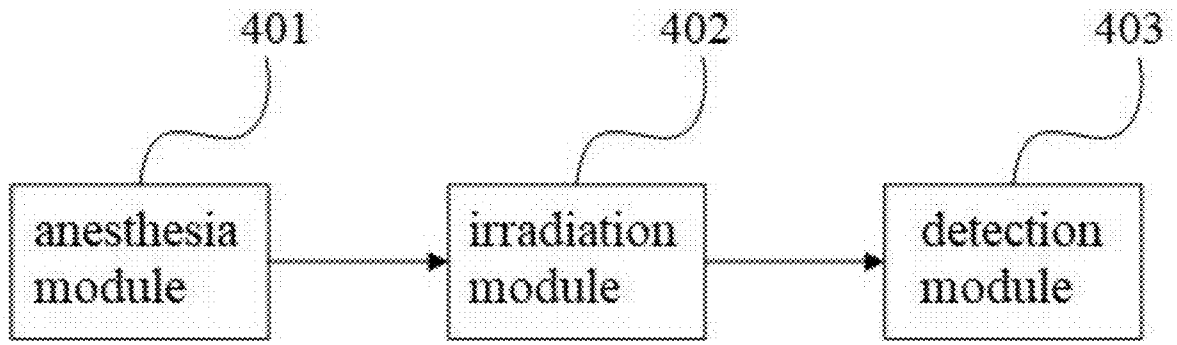
FIG. 4 is a schematic structural diagram of a test system for treating AD provided by an embodiment of the present disclosure.

FIG. 4 is a schematic structural diagram of a test system for treating AD provided by an embodiment of the present disclosure;

As shown in FIG. 4, the embodiment provides a test system for treating AD, comprising:

an anesthesia module 401, used for anesthetizing experimental animals and fixing them in a stereotaxic apparatus;

an irradiation module 402, used for irradiating the experimental animals with THz wave, wherein an irradiation power of the THz wave is 25 $mW/cm^2$;

a detection module 403, used for conducting behavioral and pathological tests on the experimental animals exposed to THz wave, thereby determining the treatment outcomes.

The specific implementation method of the test system for AD provided by the embodiment can be implemented regarding the above embodiments, and will not be repeated here.

Figure 5:
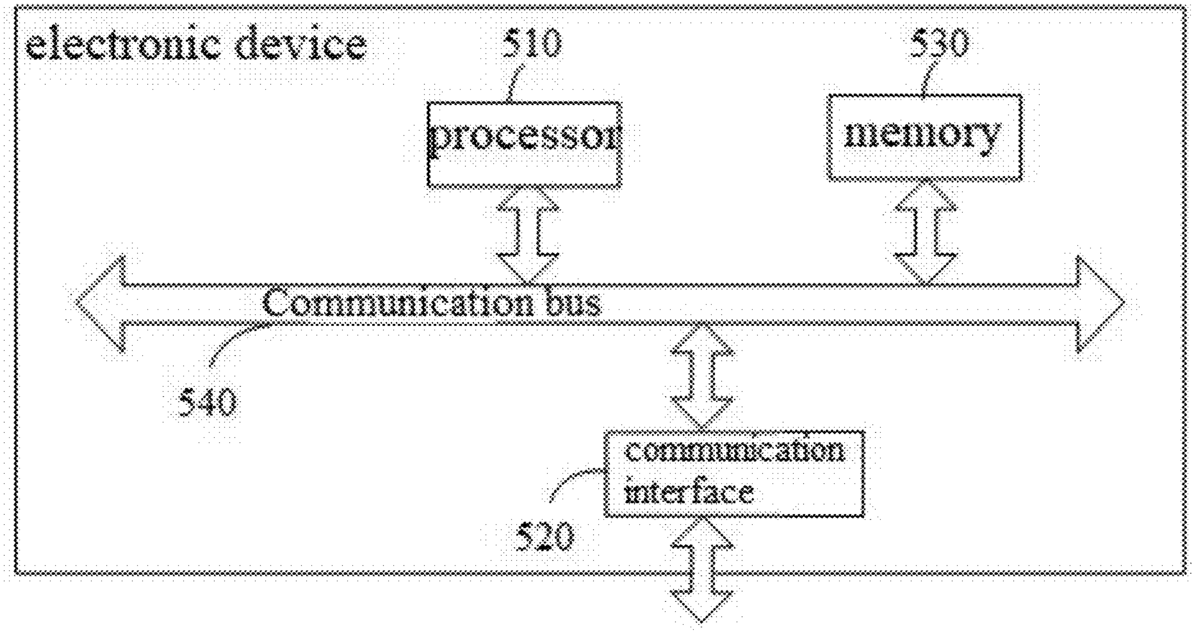
FIG. 5 is a schematic structural diagram of an electronic device provided by an embodiment of the present disclosure.
Figure 6:
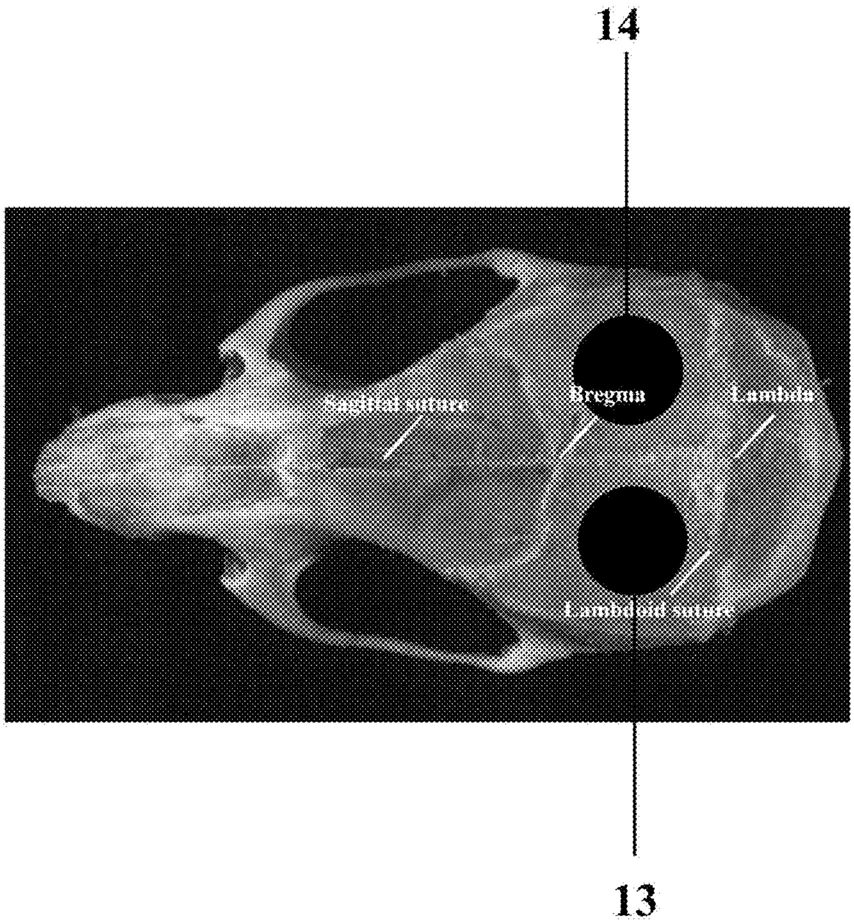
FIG. 6 is a schematic diagram of a cerebral irradiation site provided by an embodiment of the present disclosure.

FIG. 5 illustrates the physical structure of an electronic device. As shown in FIG. 5, the electronic device may comprise a processor 510, a communication interface 520, a memory 530, and a communication bus 540, wherein the processor 510, the communication interface 520, and the memory 530 communicate with each other through the communication bus 540. The processor 510 can call the logical instructions in the memory 530 to execute the test method for treating AD, which comprises:

anesthetizing experimental animals and fixing them in a stereotaxic apparatus;

irradiating the experimental animals with THz wave to obtain irradiated experimental animals, wherein an irradiation power of the THz wave is 25 $mW/cm^2$;

conducting behavioral and pathological tests on the irradiated experimental animals with THz irradiation, and determining a treatment result.

In addition, the above-mentioned logical instructions in memory 530 can be realized in the form of software functional units and can be stored in a computer-readable storage medium when they are sold or used as independent products. Based on this understanding, the technical solutions of the present disclosure may be embodied in the form of a software product, which is stored in a storage medium and comprises several instructions to make a computer device (which can be a personal computer, a server, a network device, etc.) execute all or part of the steps of the methods of various embodiments of the present disclosure. The aforementioned storage media comprise U disk, mobile hard disk, Read-Only Memory (ROM), Random Access Memory (RAM), magnetic disk or optical disk, and other media that can store program codes.

On the other hand, the disclosure also provides a computer program product, which comprises a computer program that can be stored on a non-transient computer-readable storage medium, and when the computer program is executed by a processor, the computer can execute the test method for treating AD provided by the above methods, and the method comprises:

anesthetizing experimental animals and fixing them in a stereotaxic apparatus;

irradiating the experimental animals with THz wave to obtain irradiated experimental animals, wherein an irradiation power of the THz wave is 25 $mW/cm^2$;

conducting behavioral and pathological tests on the irradiated experimental animals with THz irradiation, and determining a treatment result.

On the other hand, the present disclosure also provides a non-transient computer-readable storage medium, on which a computer program is stored, and the computer program, when executed by a processor, is realized to carry out the test method for treating AD provided by the above methods, and the method comprises:

anesthetizing experimental animals and fixing them in a stereotaxic apparatus;

irradiating the experimental animals with THz wave to obtain irradiated experimental animals, wherein an irradiation power of the THz wave is 25 $mW/cm^2$;

conducting behavioral and pathological tests on the irradiated experimental animals with THz irradiation, and determining a treatment result.

The device embodiments described above are only schematic, in which the units described as separate components may or may not be physically separated, and the components displayed as units may or may not be physical units, that is, they may be located in one place or distributed to multiple network units. Some or all of the modules can be selected according to actual needs to achieve the purpose of this embodiment. Ordinary technicians in this field can understand and implement it without creative labor.

Example 1

SPF (specific pathogen-free) grade male 5-month-old $APP^{SWE}/PS1^{DE9}$ double mutant transgenic mice were purchased from Jackson Laboratory (No. 005864). The transgenic mice were AD mice.

The feeding conditions of the experimental animals met the SPF level: temperature 22±2° C.; humidity 50±10%; ventilation every 20 minutes; 12 h/12 h light/dark cycle alternately, the light time is from 7 am to 7 pm, and food and water were freely available. $APP^{SWE}/PS1^{DE9}$ mice were genotyped by polymerase chain reaction (PCR) amplification of genomic DNA extracted from tail snips.

Figure 7:
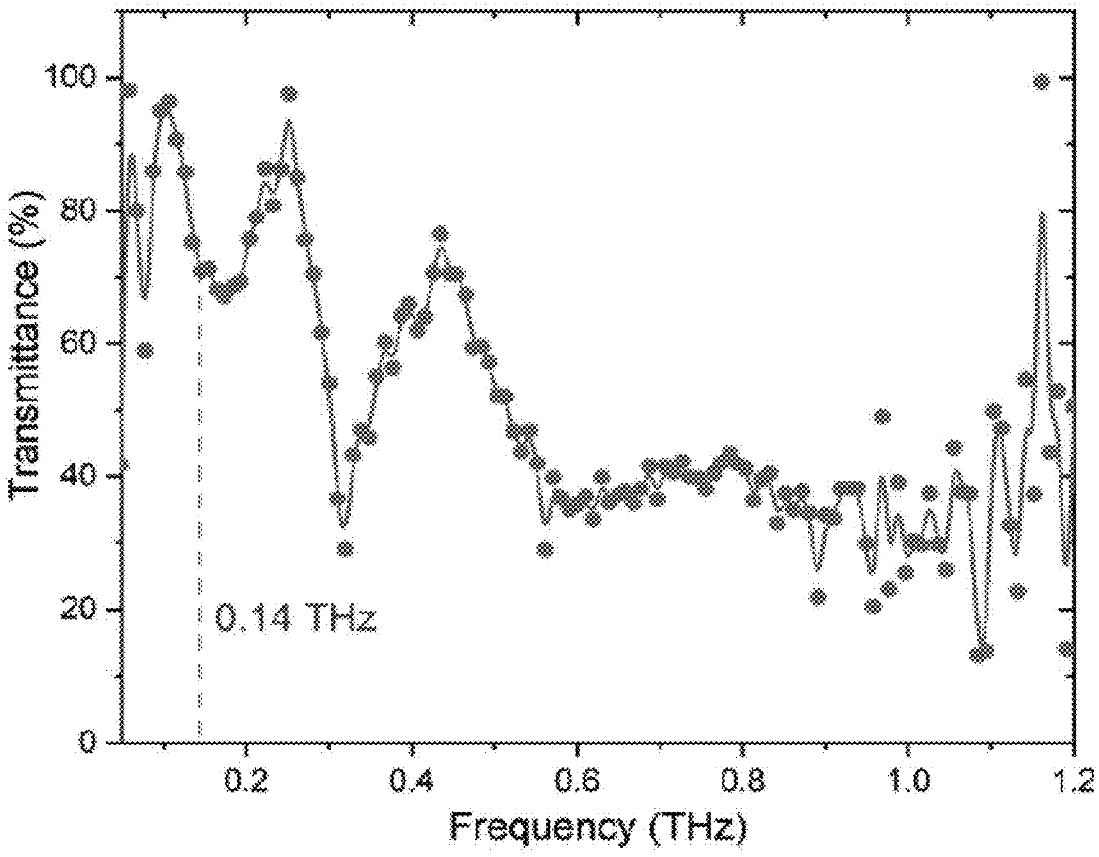
FIG. 7 is a schematic diagram of the skull penetration rate of THz wave provided by an embodiment of the present disclosure.

Experiments were carried out on mice through the test method and device for AD provided by the disclosure, THz wave was generated by a generator (RFPA S.A, MODEL RFS9001800-25), which can generate a pulse frequency of 0.14 THz at an average power of 100 mW. THz wave emitted by the THz source was fed into a horn antenna and collimated using a TPX lens to obtain a beam. The transmission efficiency of the fiber is 10%, which means the power reaching the tail end of the fiber is 10 mW. The diameter of the optical fiber is less than 3 mm. Considering that the optical fiber initially irradiates to the mouse head with a certain degree of divergence, the optical spot is assumed to be 5 mm (upper limit), so the irradiation area is 19.63 $mm^2$ (~0.1963 $cm^2$). For the convenience of calculation, it is regarded as 0.2 $cm^2$. The power density is 10 mw/0.2 $cm^2$=50 $mW/cm^2$. Considering the pulse factor, the final power density of the fiber terminal is 25 $mW/cm^2$. In this experiment, 10 min was finally chosen to irradiate mice. Animals were exposed to low-frequency THz wave (0.14 THz, 10 min per day at 8 P.M., 5 days per week for 12 consecutive weeks), the mice obtained were marked as 'AD-THz' in FIGS. 8A-13J. An infrared thermal imager monitored the temperature changes of experimental animals. As shown in FIG. 7, the percentage of THz wave penetration across the skull of a mouse is ~70%, which guarantees that THz wave can penetrate calvaria and act on the relevant brain regions.

Example 2

The only difference between Example 2 and Example 1 was that the experiment was carried out with age- and gender-matched wild-type (WT) littermates, the mice obtained were marked as 'WT-THz' in FIGS. 8A-13J.

Example 3

The only difference between Example 3 and Example 1 was that transgenic mice were anesthetized with isoflurane and subjected to sham stimulation by turning off the stimulated signal for treating AD provided by the disclosure, the mice obtained were marked as 'AD-Ctrl' in FIGS. 8A-13J.

Example 4

The difference between Example 4 and Example 1 was that wild-type (WT) mice were used, and the mice were anesthetized with isoflurane and subjected to sham stimulation by turning off the stimulated signal for treating AD provided by the disclosure, the mice obtained were marked as 'WT-Ctrl' in FIGS. 8A-13J.

As described previously[1, 2], the mice in Examples 1-4 were subjected to the Morris water maze test, Y-maze test, and open field test in order. In order to avoid the influence of stress factors on the experimental results, we placed the mice in the behavioral laboratory one week before behavioral tests to make the mice familiar with the laboratory environment. Mice were sacrificed after the behavioral test, then to conduct immunofluorescent staining, western blotting, and enzyme-linked immunosorbent assay, and the results were analyzed.

Among them, the Morris water maze test was a behavioral experimental method to test the spatial exploration, learning, and memory of mice. The Morris water maze test consisted of three platform trials per day for 4 consecutive days, followed by a probe trial. The escape latency was measured in platform trials. The number of platform crossings in the target quadrant and time spent in this quadrant were measured in probe trials. All of the behavioral parameters of the mice were tracked, recorded, and analyzed using SMART 3.0 software (Harvard Apparatus).

The Y-maze test was used to evaluate the spatial learning and memory of mice. Y-maze consists of three arms, each of which is 30 cm long×10 cm wide×20 cm high, and is labeled as A, B, and C arms respectively. The mice were placed in the middle of the Y maze and allowed to move freely through the Y-maze during a 6-min session. The sequence and total times of mice entering each arm were recorded by camera and Supermaze software (XR-X Maze, Shanghai Xin Ruan Information Technology Co., Ltd., China). If a mouse enters three different arms continuously, the number of alternations will be recorded once, such as A-B-C, B-C-A, C-A-B, A-C-B, C-B-A, B-A-C. The percentage of alternation was calculated as R (%)=the total number of alternations×100/(total number of arm entries−2)×100%, and the total number of arm entries >10 can be included in the data. The Y maze was wiped with 75% ethanol after each time.

The open-field test was performed in a quiet testing room. To measure the locomotor activity, mice were placed into an Activity Monitor instrument (25×25×30 cm, Med Associates Inc., St. Albans, USA) equipped with computer-controlled photocells. Locomotor activity was automatically recorded for 20 min, and the total distance traveled and the number of rearings was calculated by the Med system.

Immunofluorescent staining experiments comprise:

After the behavioral tests, the mice were anesthetized and transfused with phosphate-buffered saline (PBS; Boster, China). The brains were quickly removed and post-fixed with 4% paraformaldehyde overnight. Brain tissues were then incubated in 30% sucrose in PBS for cryoprotection, and 40 μm serial sections were prepared using Leica cryostat (CM-1950S, Leica, Germany). Sections were next incubated with blocking buffer (10% normal goat serum, 1% bovine serum albumin, and 0.3% Triton X-100, PBS solution) overnight at 4° C. and then incubated with the primary antibodies overnight at 4° C. (Table 1). The stained sections were imaged using a laser scanning confocal microscope (A1 confocal, Nikon Instruments (Shanghai) Co., Ltd). The paired images in the figures were collected at the same gain and offset settings. For ThioS staining, sections were stained with 0.05% ThioS (23059, AAT Bioquest) in 50% ethanol in the dark for 8 min at room temperature, followed by two rinsing in 80% ethanol for 10 s each. Immunofluorescence images were acquired using a fluorescent microscope (Olympus) and analyzed using the ImageJ software.

TABLE 1

Antibodies used in this study.

| Target | Species | Application | Dilution | Company | Cat. number |
|---|---|---|---|---|---|
| MAP-2 | Rabbit | IFC | 1:200 | abcam | ab183830 |
| NeuN | Mouse | IFC | 1:500 | Merck | MAB377 |
| p-tau S396 | Rabbit | IFC | 1:1000 | abcam | ab109390 |
| p-tau S396 | Rabbit | WB | 1:1000 | abcam | ab109390 |
| Tau5 | Mouse | WB | 1:1000 | abcam | ab80579 |
| Synaptophysin | Rabbit | IFC | 1:1000 | abcam | ab32127 |
| GAPDH | Rabbit | WB | 1:4000 | CST | 2118 |

Western blotting experiment comprises:

Mice were sacrificed after the behavioral test, and the tissues were dissected rapidly on ice and homogenized in cold RIPA buffer (Beyotime Biotechnology, Shanghai, China) containing protease and phosphatase inhibitor cocktails (Sigma-Aldrich, St. Louis, MO, USA) and then lysed for 30 min on ice. The protein concentration in the supernatant was determined using protein assay kits (TaKaRa, Shiga, Japan). Forty micrograms of protein were loaded and separated by sodium dodecyl sulfate/polyacrylamide gel electrophoresis and then transferred to polyvinylidene fluoride membranes (Millipore, Bedford, MA, USA). After blocking, membranes were incubated with appropriate primary antibodies (Table 1) at 4° C. overnight, followed by 1 h incubation at room temperature with a peroxidase-conjugated secondary antibody. Finally, the membrane was incubated with enhanced chemiluminescence (Millipore, Bedford, MA, USA), and the target protein bands were quantified using the FluorChem Q system (ProteinSimple, California, USA).

Enzyme-linked immunosorbent assay can measure the concentrations of Aβ40 and Aβ42 (Elabscience, e-El-H0542c to detect Aβ40, and e-El-H0543c to detect Aβ42) in brain tissue extract by ELISA according to the manufacturer's instructions.

The results are presented as the mean±SEM. As applicable, statistical comparisons between the two groups were made using the Student's t-test or the Mann-Whitney U-test. One-way ANOVA and Tukey's test were used to compare four groups. P values less than 0.05 (two-sided) were considered significant. All analyses were performed with GraphPad Prism software, version 9.0.

Figure 8A:
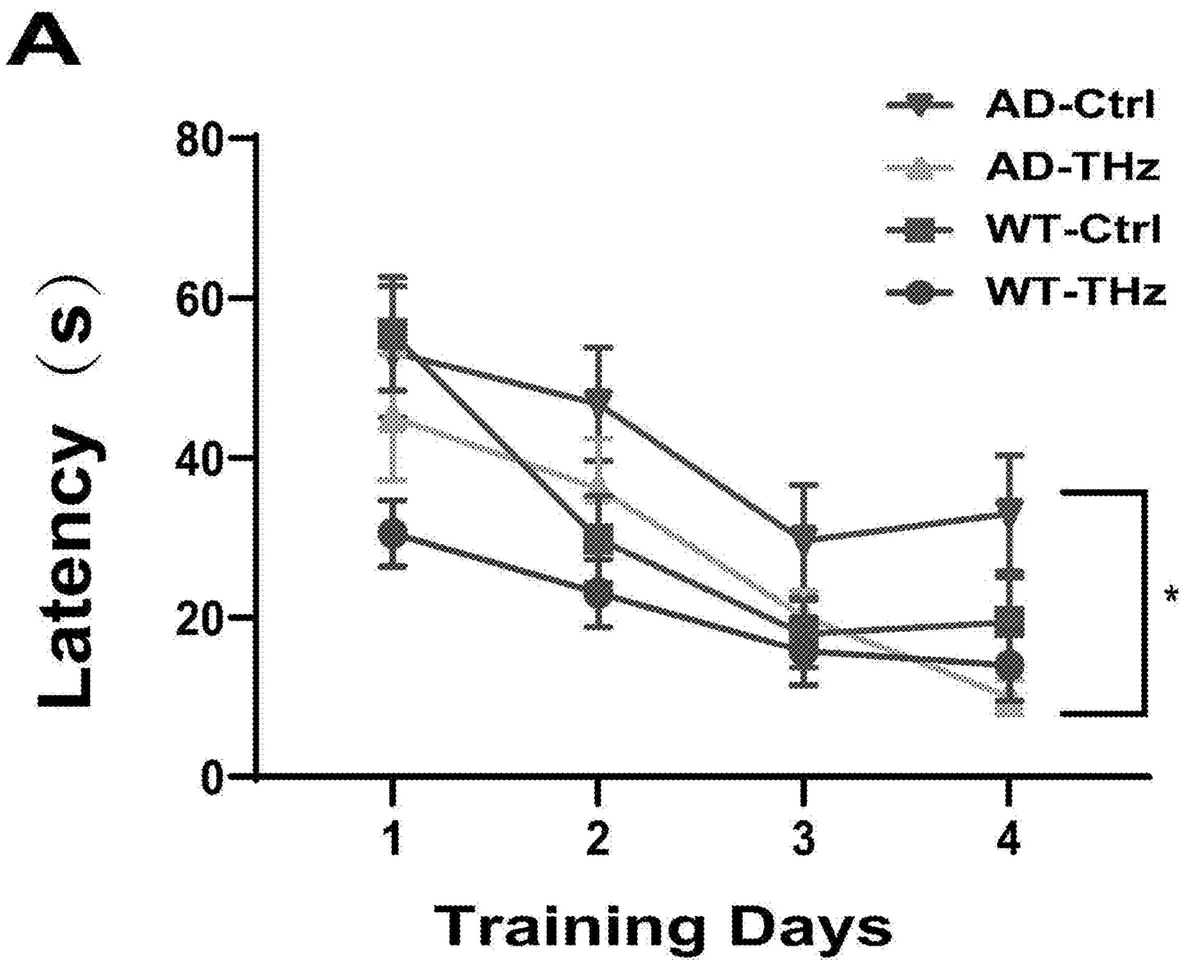
FIGS. 8A-8C are schematic diagrams of long-term memory performances in mice after THz irradiation provided by an embodiment of the present disclosure.
Figure 8B:
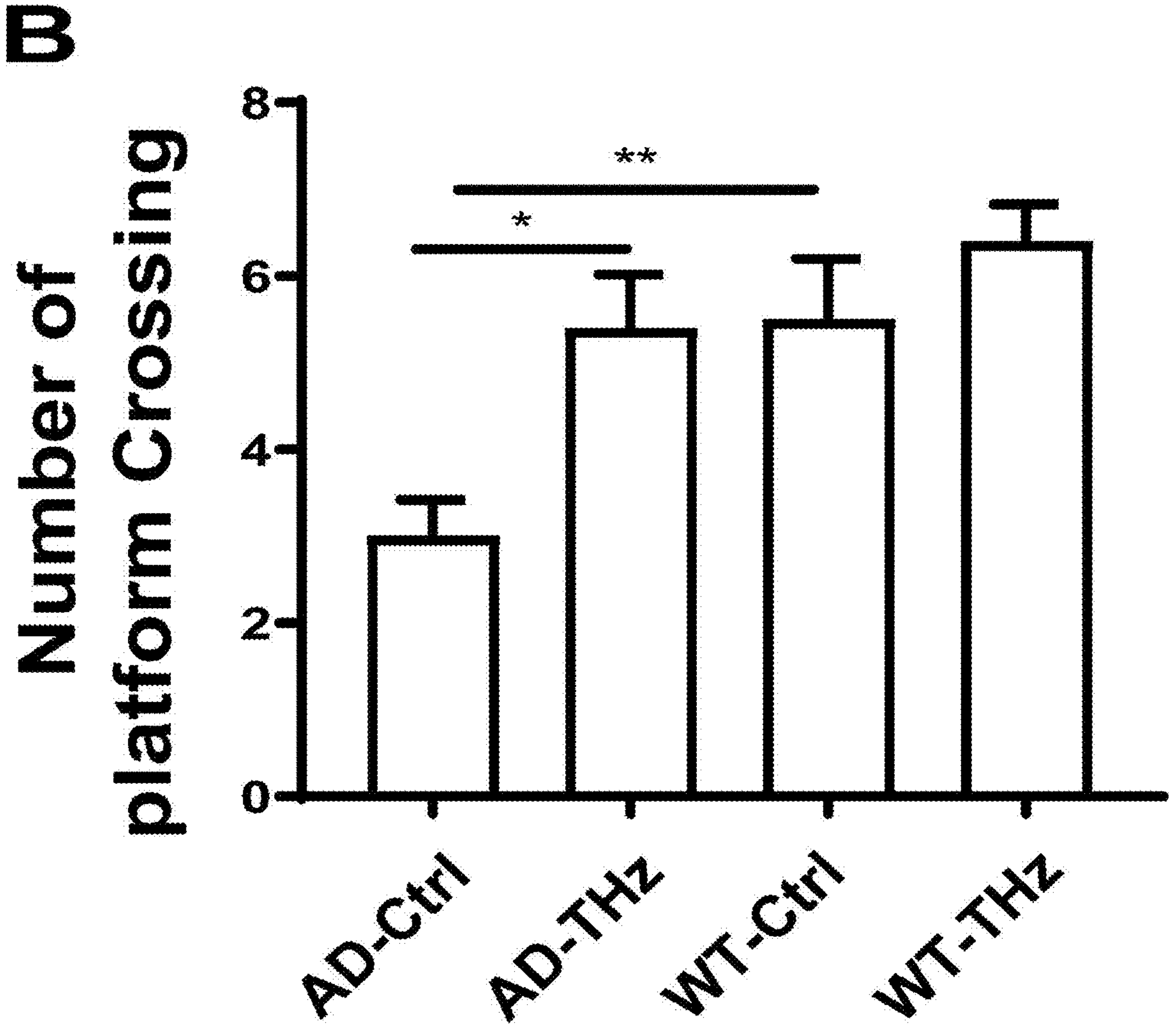
Figure 8C:
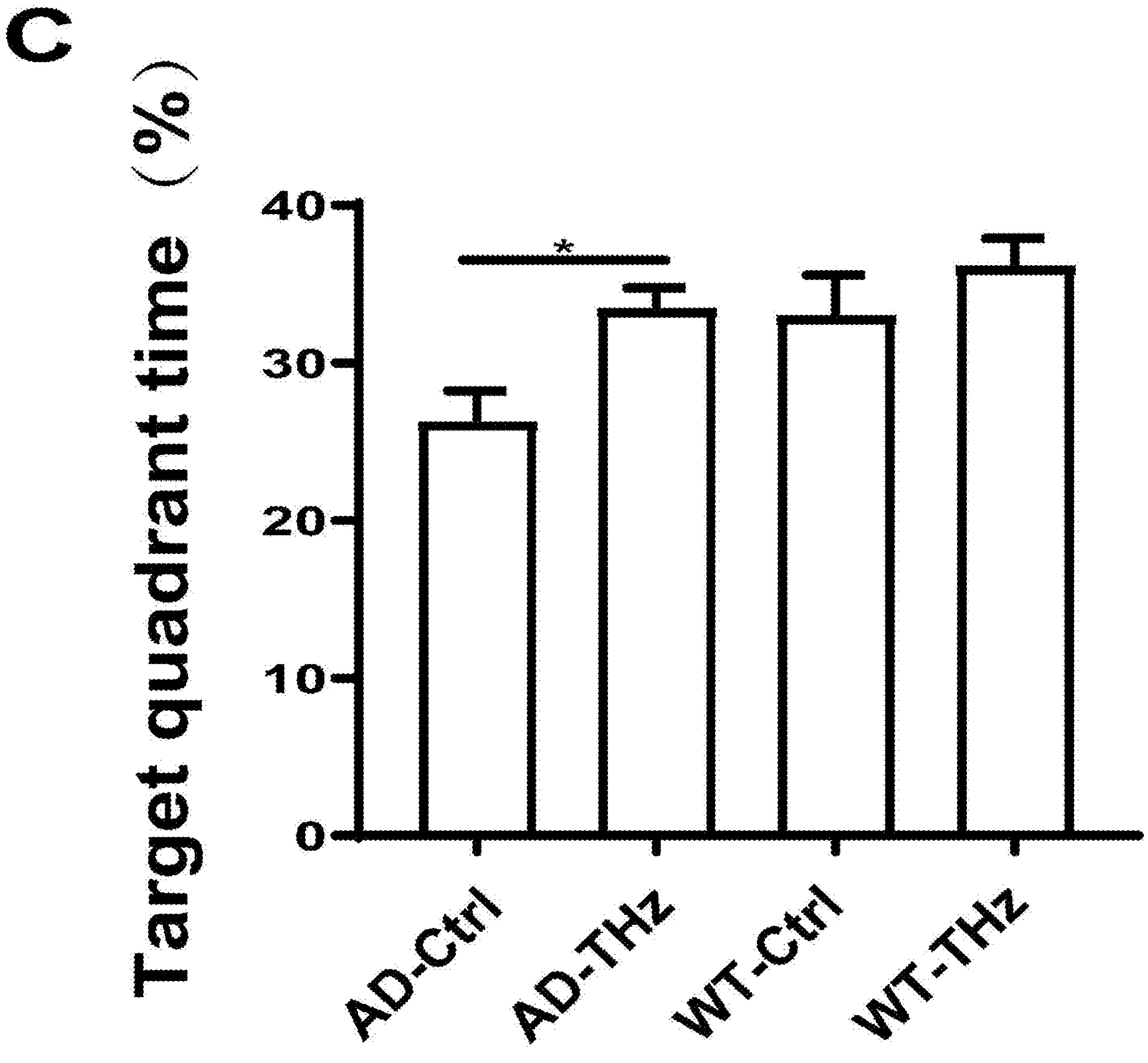

FIGS. 8A-8C are schematic diagrams of the long-term memory performances of mice after THz irradiation provided by an embodiment of the present disclosure.

Figure 9:
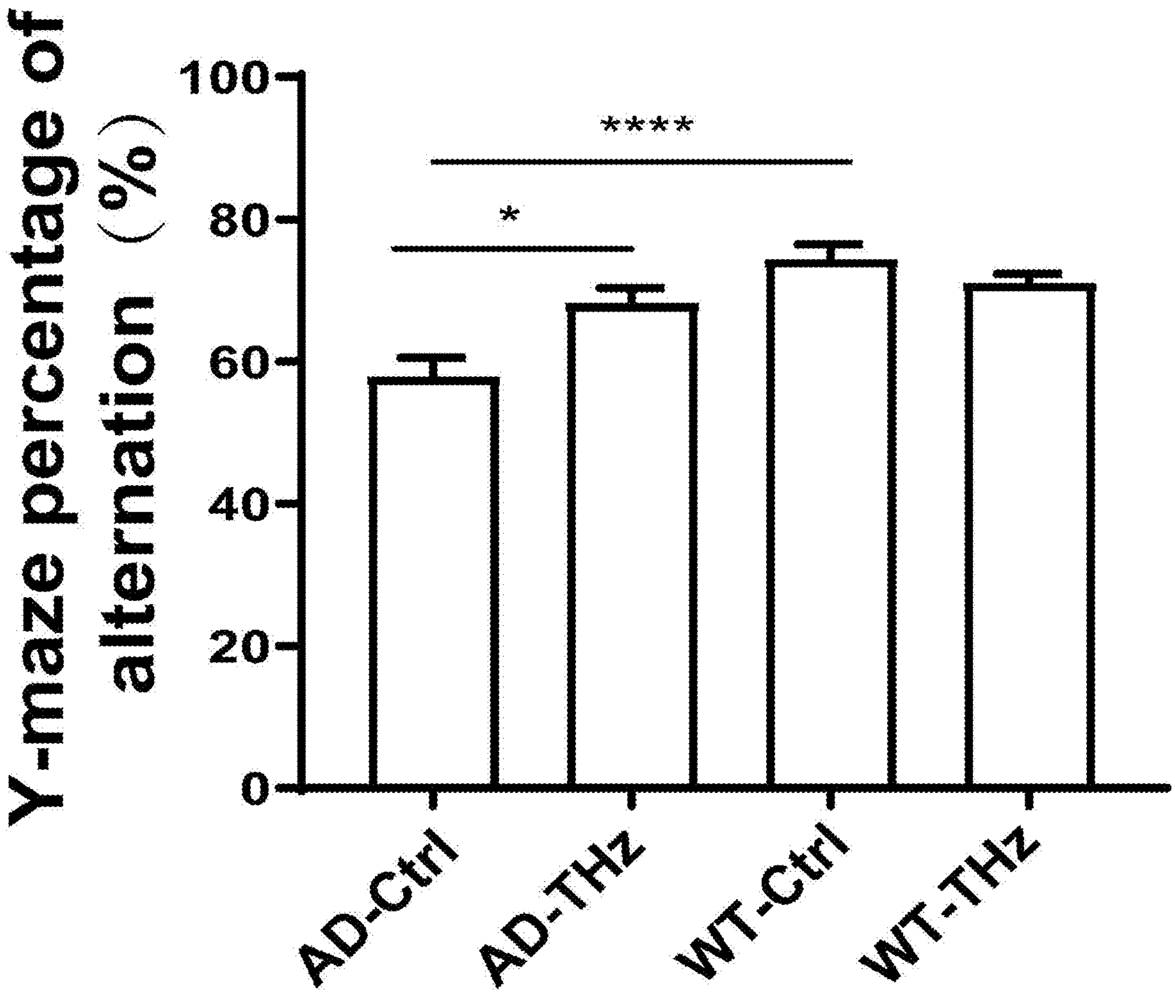
FIG. 9 is a schematic diagram of short-term memory performances in mice after THz irradiation provided by an embodiment of the present disclosure.

FIG. 9 is a schematic diagram of the short-term memory performances of mice after THz irradiation provided by an embodiment of the present disclosure.

According to the experimental results, compared with the WT mice in Example 4, the AD mice in Example 3 showed a significant cognitive decline in spatial learning, as shown in FIG. 8A by a significantly longer escape latency compared with the WT mice in Example 4. Compared with the AD mice in Example 3, the escape latency of the AD mice with THz irradiation in Example 1 was significantly shortened; compared with the WT mice in Example 4, the AD mice in Example 3 crossed the target quadrant less often and spent less time in the target quadrant ($p<0.01$) in cross numbers and 20% reduction of time in the target quadrant, indicating that spatial memory consolidation was impaired, as shown in FIGS. 8B and 8C. Compared with the AD mice in Example 3, the AD mice with THz irradiation in Example 1 spent significantly more time in the target quadrant and showed increased crossovers (both $p<0.05$; FIG. 8B and FIG. 8C), suggesting an improved cognitive function.

Consistently, in Y-maze test, compared with the WT mice in Example 4, the AD mice in Example 3 showed a relatively lower alternation rate ($p<0.0001$; FIG. 9). However, the AD mice with THz irradiation in Example 1 showed a relatively higher alternation rate in the Y-maze test compared with the AD mice in Example 3 ($p<0.05$; FIG. 9) in alternation rate, implying an ameliorating effect of THz treatment on the cognitive impairment in AD.

Figure 10A:
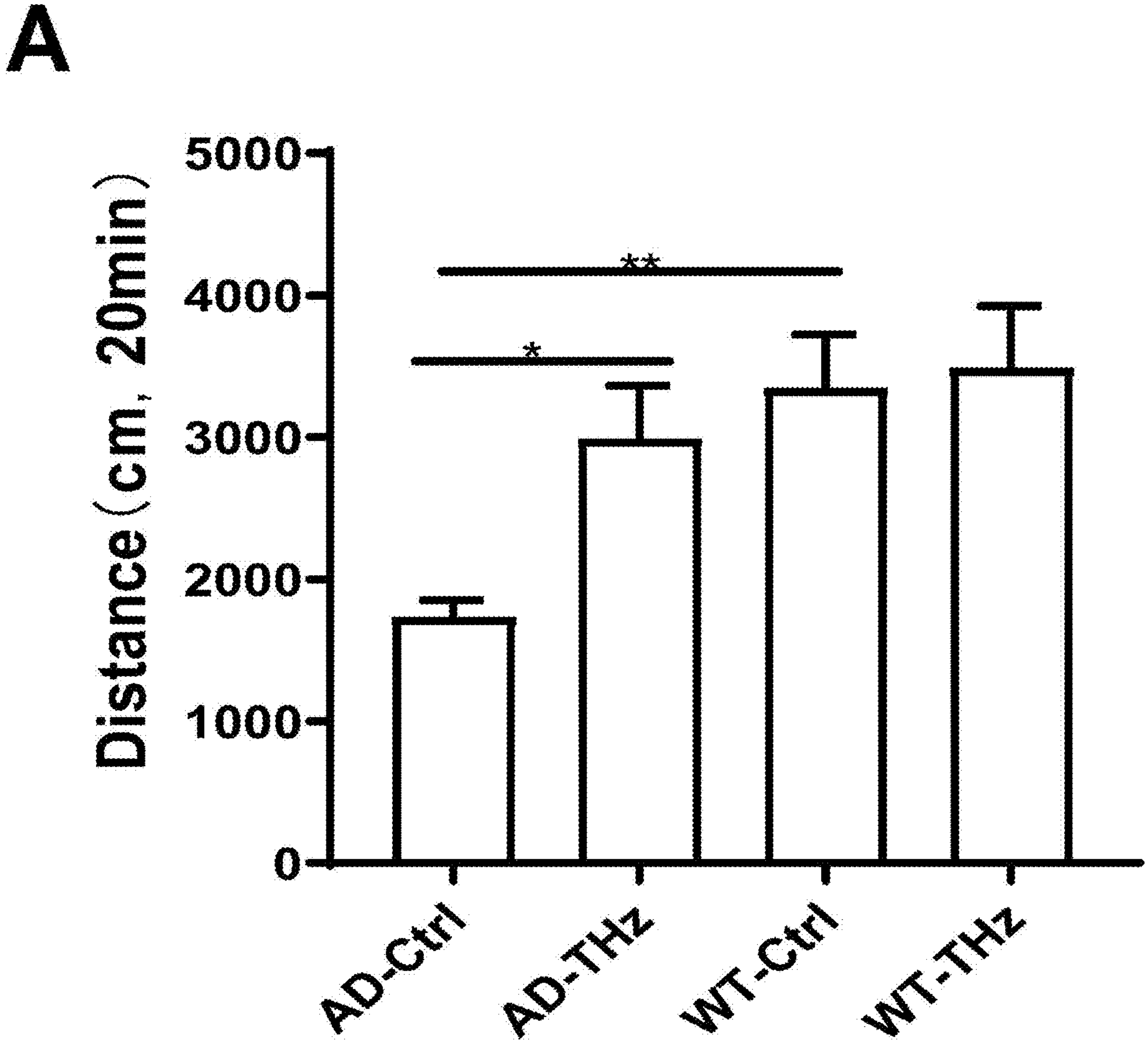
FIGS. 10A-10B are schematic diagrams of spatial exploration ability performances in mice after THz irradiation provided by an embodiment of the present disclosure.
Figure 10B:
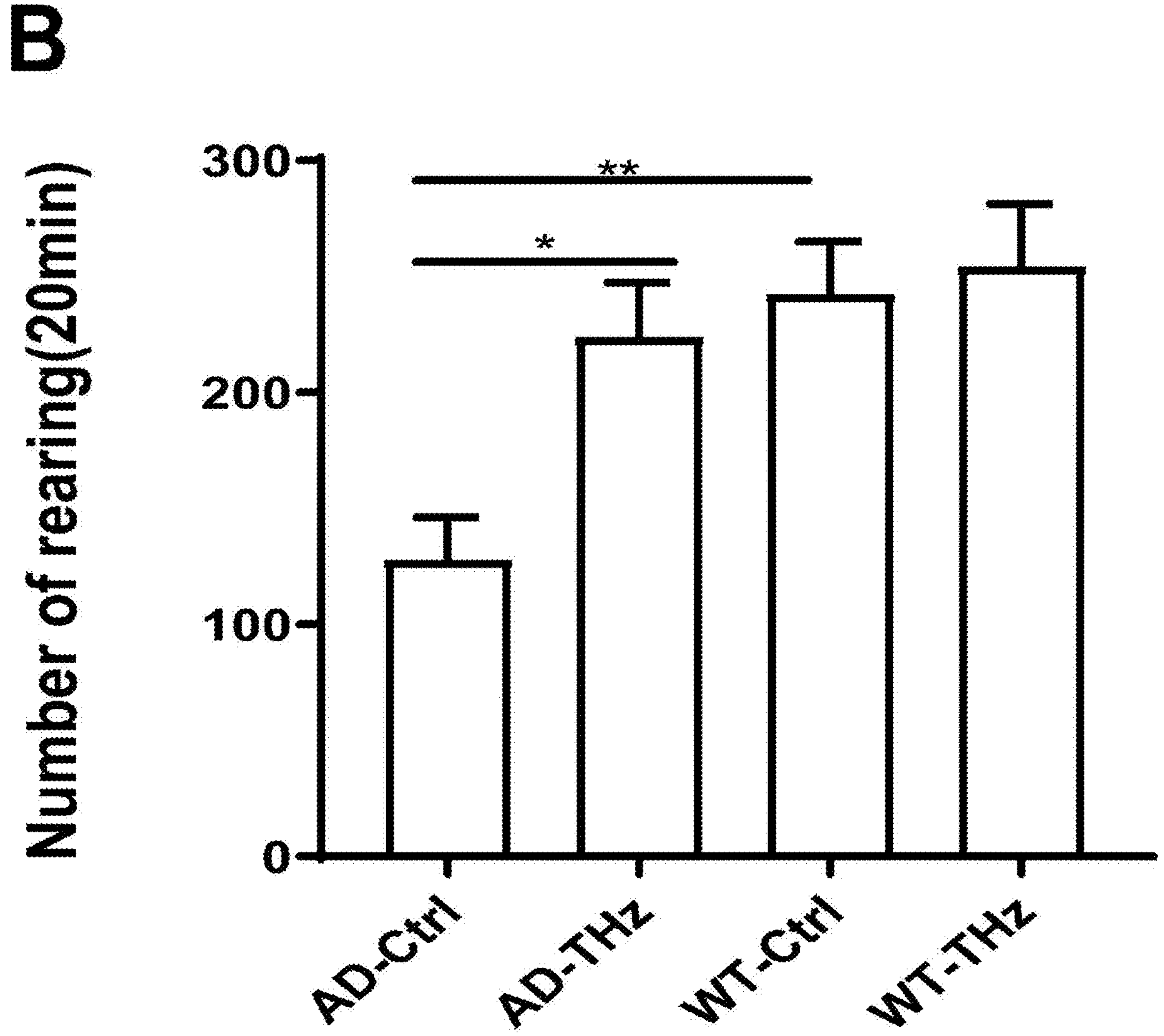

FIGS. 10A-10B are schematic diagrams of the spatial exploration ability performances of mice after THz irradiation provided by an embodiment of the present disclosure.

Compared with the WT mice in Example 4, the AD mice in Example 3 showed a relatively lower exploration distance and numbers of rearing (both $p<0.01$; FIGS. 10A and 10B). Compared with the AD mice in Example 3, the AD mice with THz irradiation in Example 1 showed a relatively higher exploration distance and numbers of rearing (both $p<0.05$; FIG. 10A and FIG. 10B), suggesting an improved capacity for exploration.

FIGS. 11A-11E are schematic diagrams of Aβ pathological changes in the brain of AD mice after THz irradiation provided by an embodiment of the present disclosure.

Figure 11A:
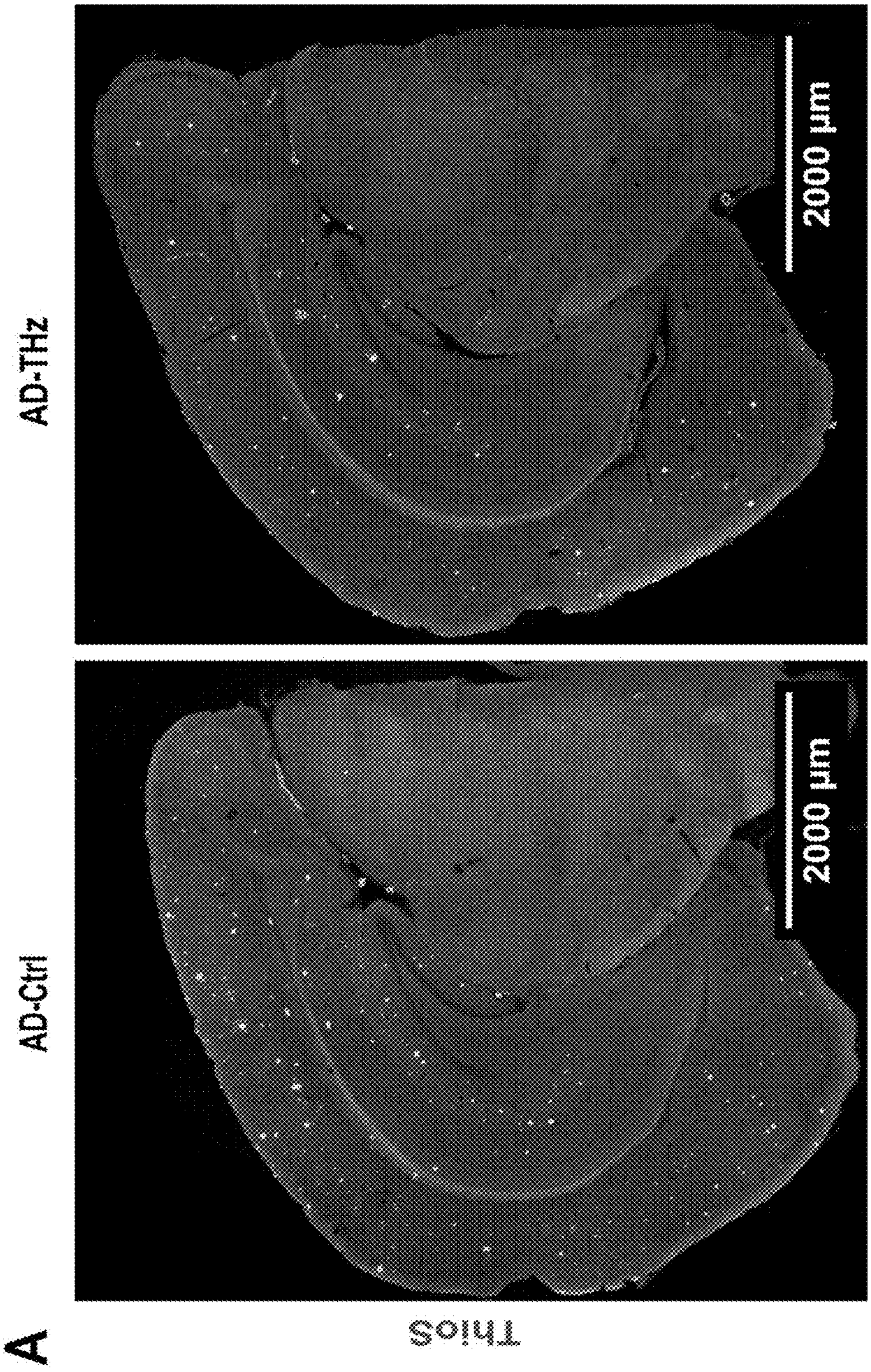
FIGS. 11A-11E are schematic diagrams of Aβ pathological changes in the brain of AD mice after THz irradiation provided by an embodiment of the present disclosure.
Figure 11B:
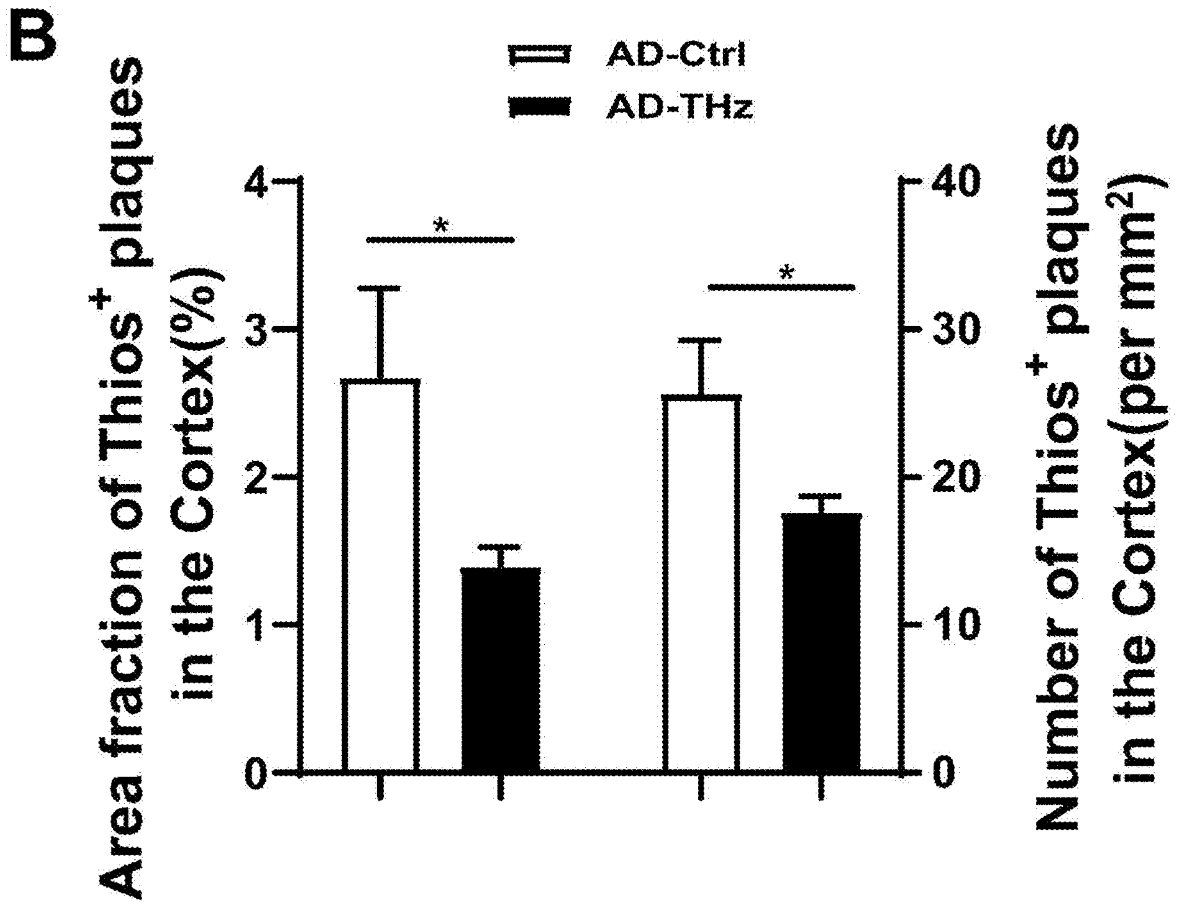
Figure 11C:
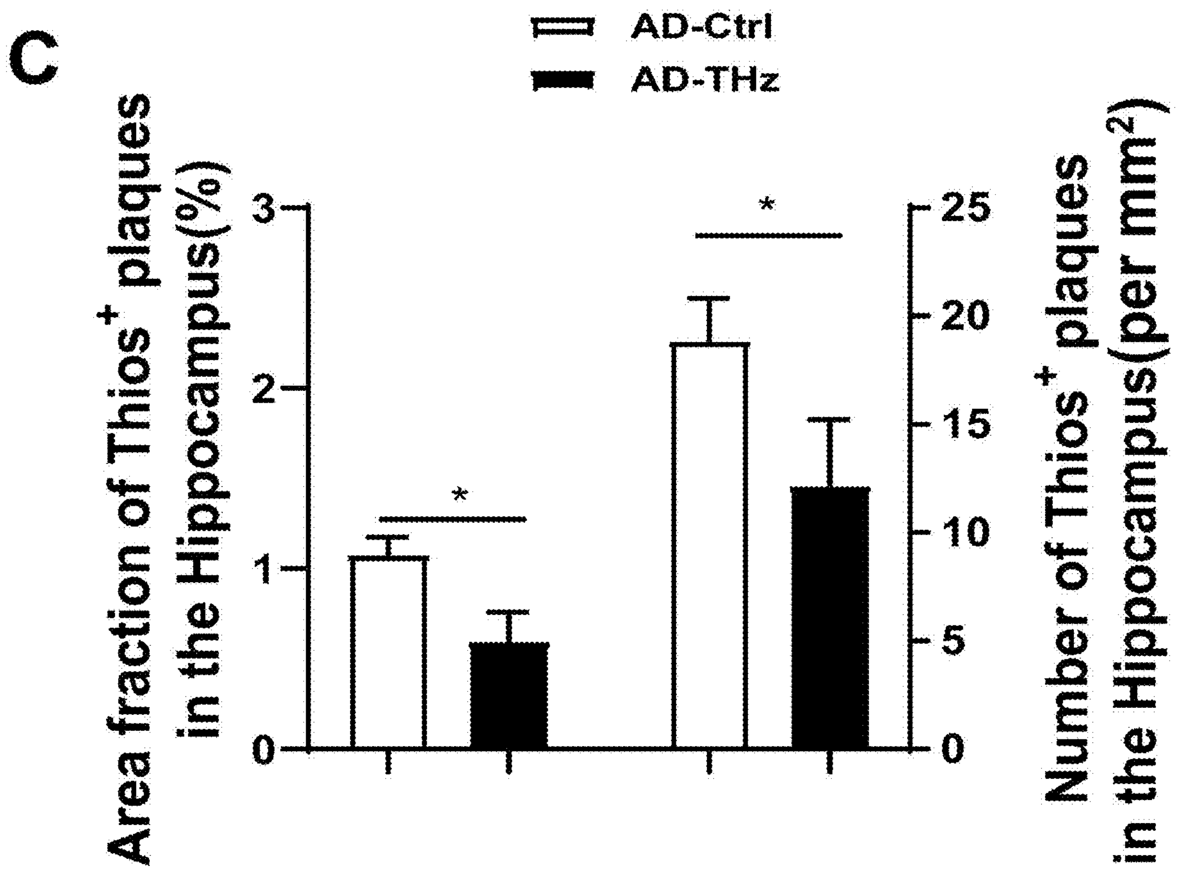
Figure 11D:
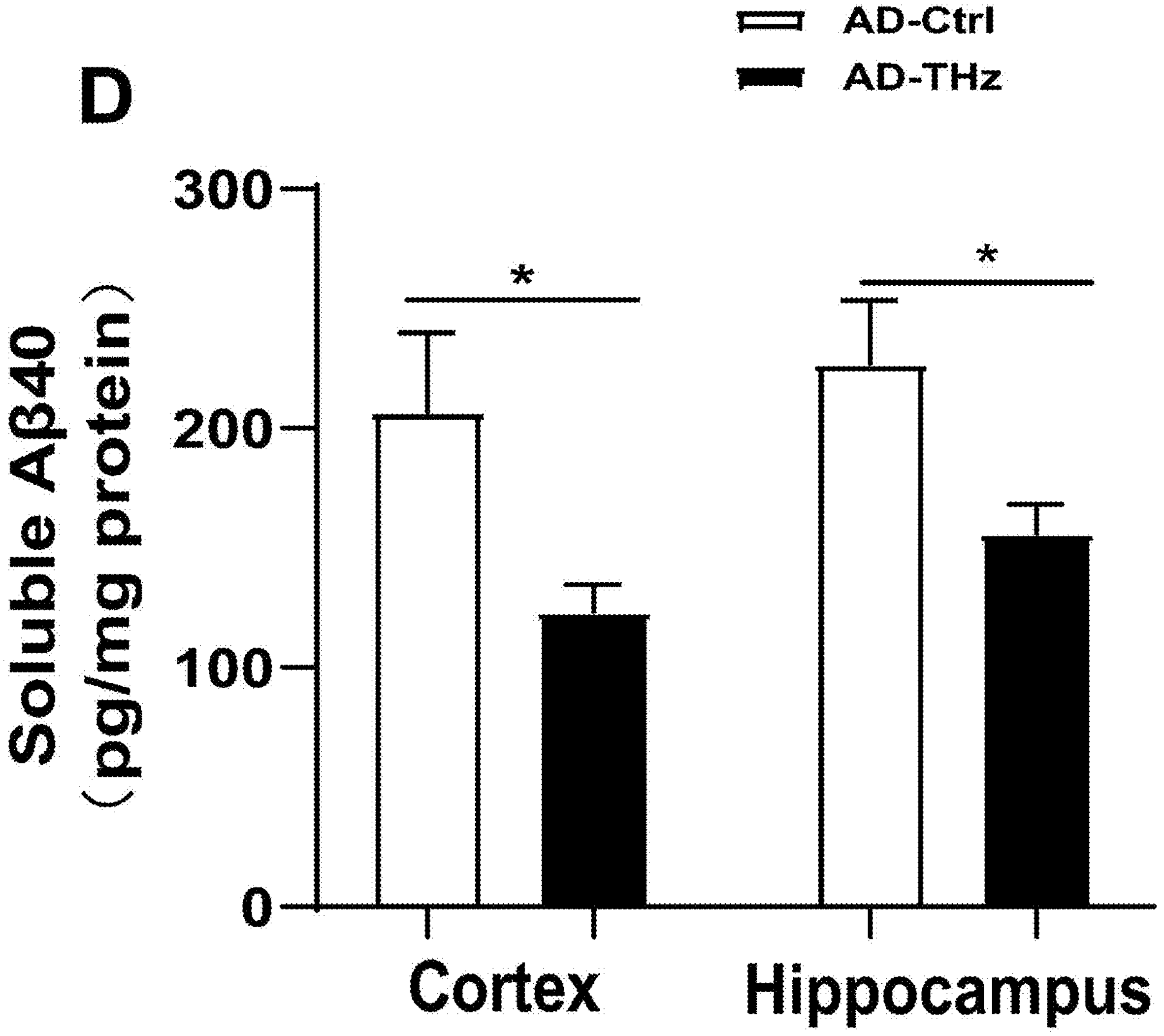
Figure 11E:
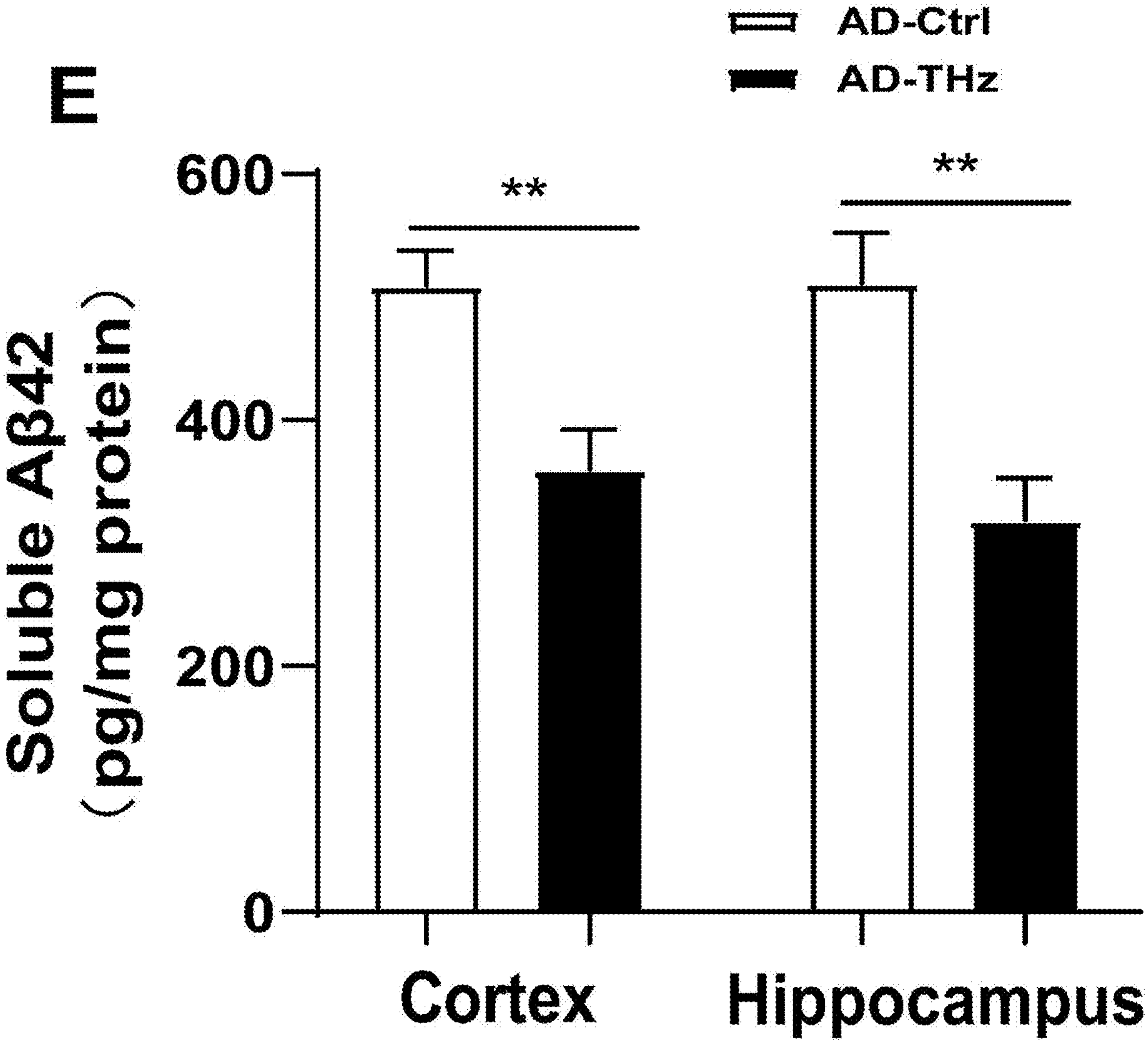

Aβ plaques are considered the primary pathological hallmark of AD, and Aβ load is often used as a biomarker for AD severity[3]. In our study, Aβ immunofluorescence staining was performed for quantification of Aβ plaques. The AD mice in Example 3 showed abundant Aβ plaque depositions in the cortex and hippocampus at 8 months of age (FIG. 11A). Immunofluorescence with ThioS staining revealed a significant decrease in the area fraction and plaque density of insoluble Aβ plaques in both the cortex (both $p<0.05$; FIG. 11B) and hippocampus (both $p<0.05$; FIG. 11C) of the AD mice with THz irradiation in Example 1, compared with the AD mice in Example 3. Consistent with these data, ELISA showed significantly lower levels of $A\beta_{40}$ and $A\beta_{42}$ in the brain homogenates extracted from the AD mice with THz irradiation in Example 1, compared with the AD mice in Example 3 (respectively, $p<0.05$; $p<0.01$; FIG. 11D and FIG. 11E) in the cortex. In the hippocampus, there was also a reduction of Aβ40 and Aβ42 (respectively, $p<0.05$; $p<0.01$; FIG. 11D and FIG. 11E). These data demonstrate that THz treatment can reduce Aβ levels and suppress the formation of Aβ plaques in the AD brain.

FIGS. 12A-12F are schematic diagrams of pathological changes of tau hyperphosphorylation in the brain of mice after THz irradiation provided by an embodiment of the present disclosure.

Figure 12A:
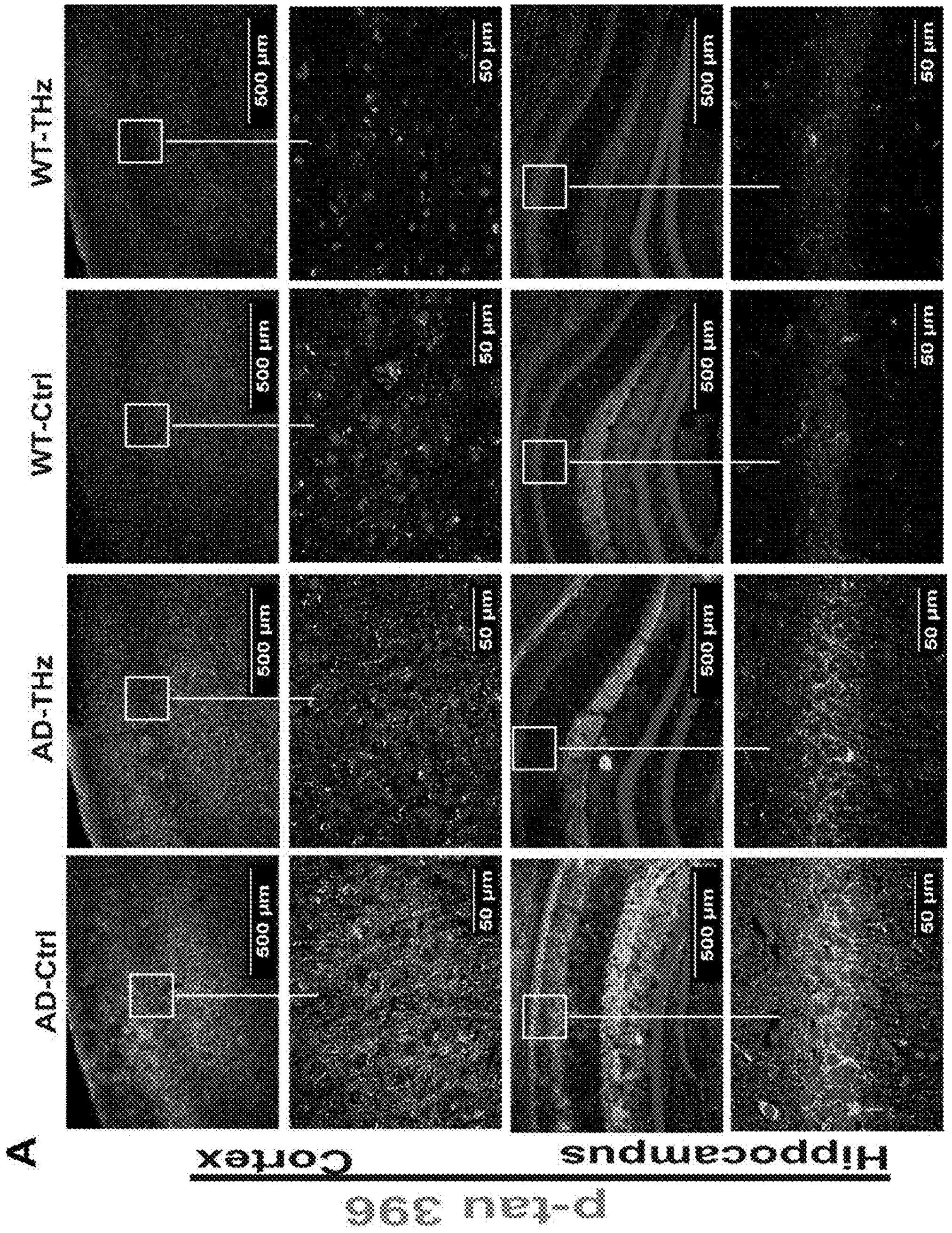
FIGS. 12A-12F are schematic diagrams of pathological changes of tau hyperphosphorylation in the brain of mice after THz irradiation provided by an embodiment of the present disclosure.
Figure 12B:
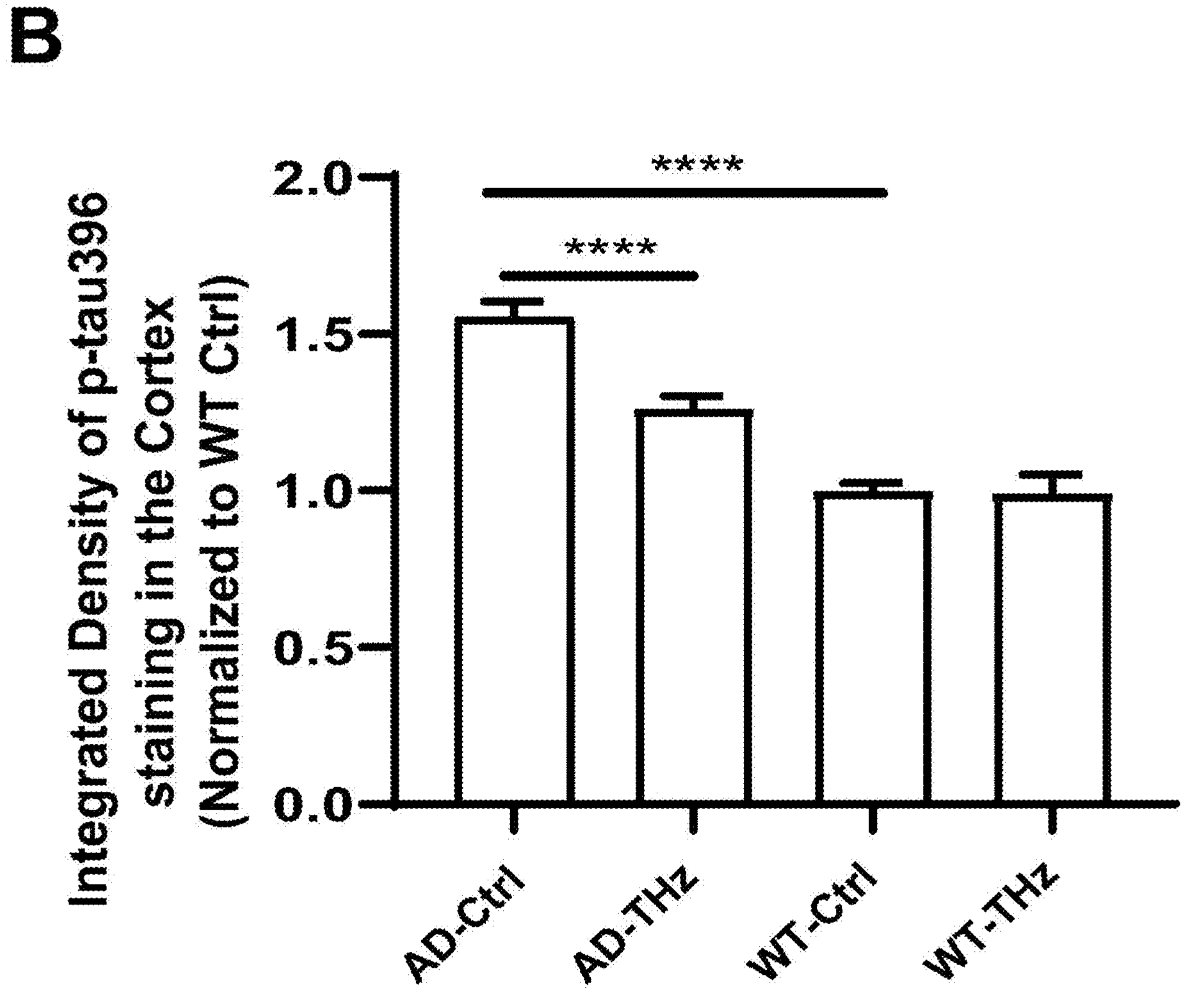
Figure 12C:
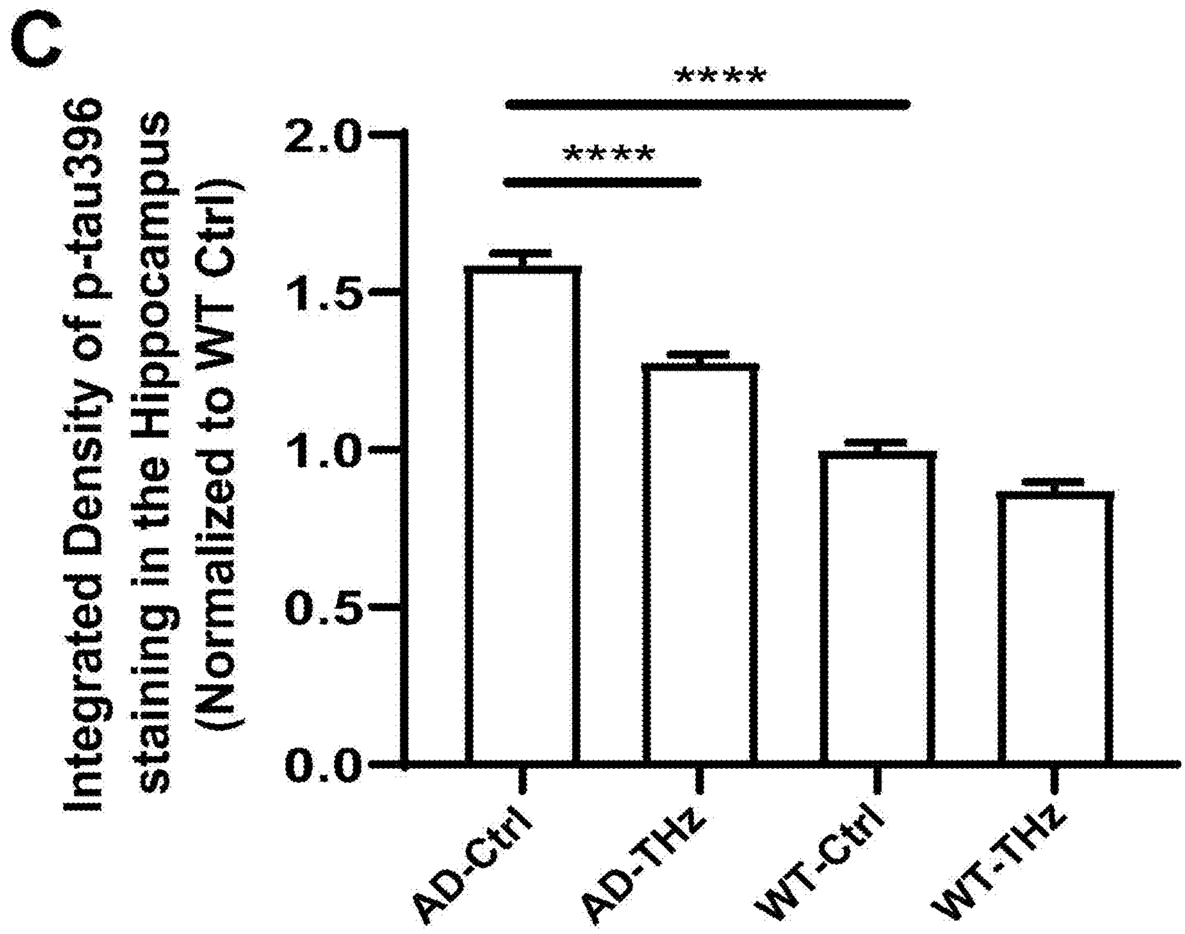
Figure 12D:
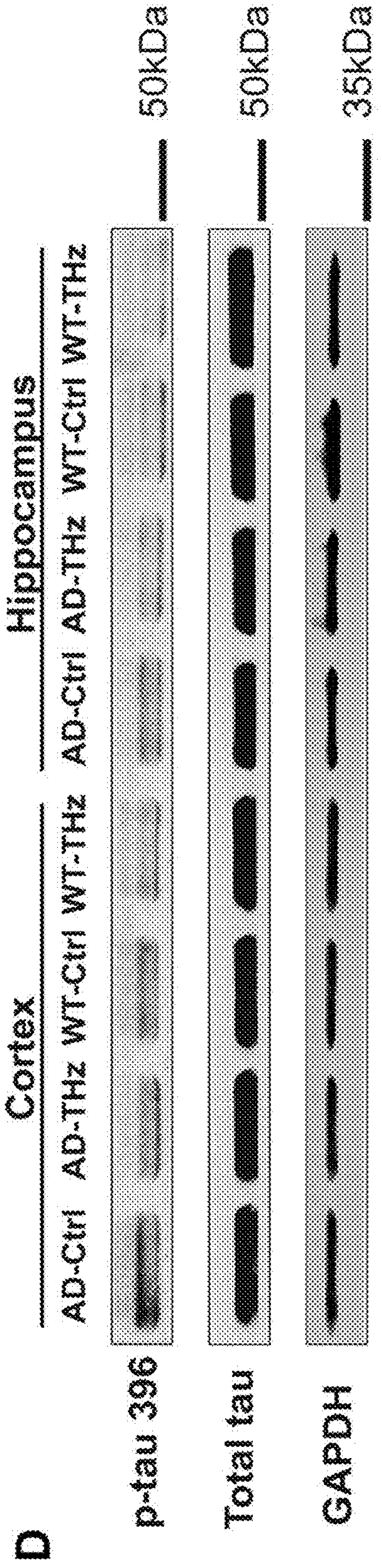

We next measured the effects of THz wave on tau hyperphosphorylation, which is another key event in AD, resulting in the formation of neurofibrillary tangle as the second pathological hallmark of AD [4]. Compared with the WT mice in Example 4, the AD mice in Example 3 showed much more disease-related p-tau 396 positive neurons in the cortex and hippocampus (both $p<0.0001$; FIG. 12B and FIG. 12C). However, the disease-related p-tau 396 positive neurons in the cortex and hippocampus of AD mice with THz irradiation in Example 1 were considerably less than those of AD mice in Example 3 (both $p<0.0001$; FIG. 12B and FIG. 12C).

Figure 12E:
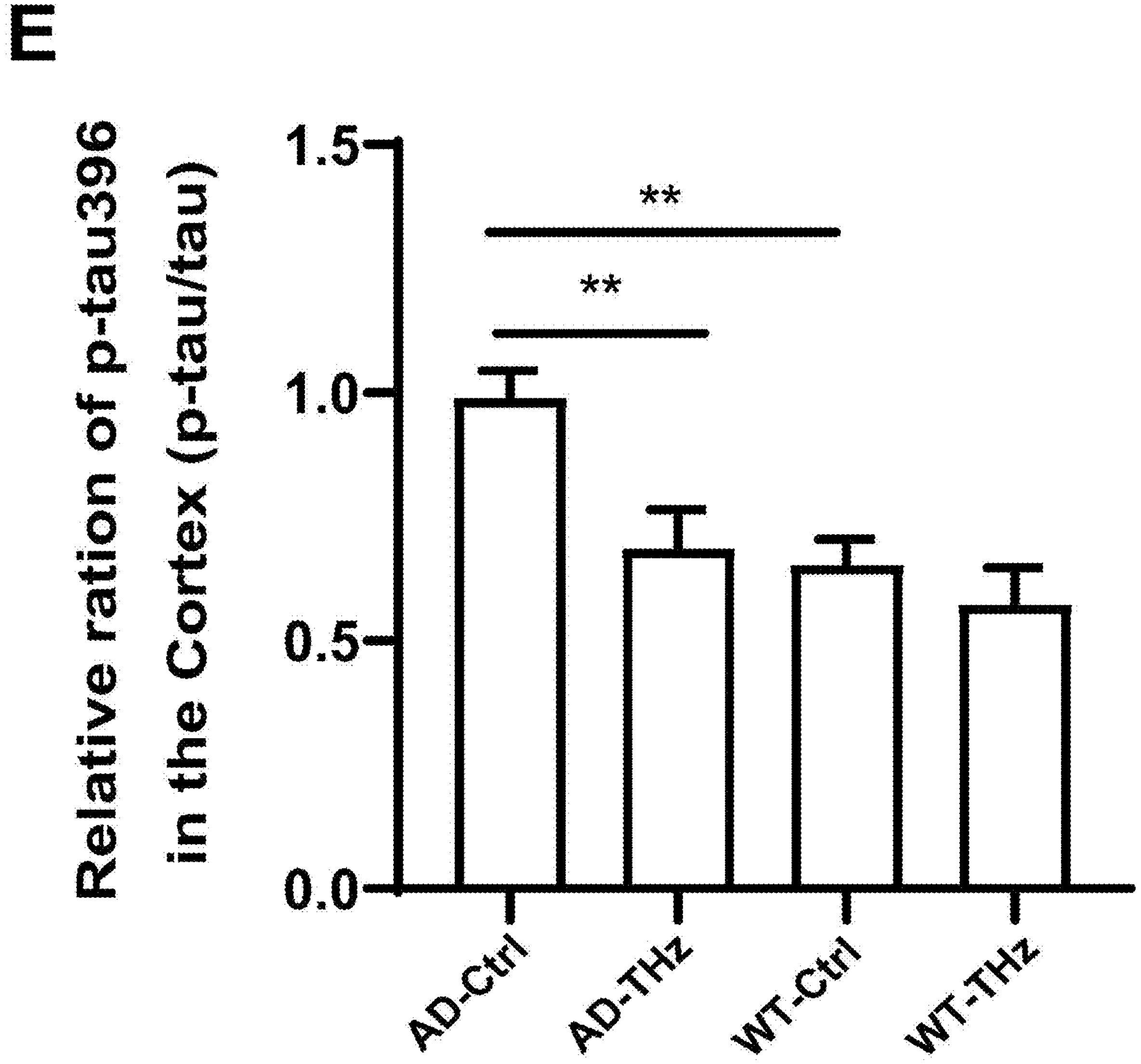
Figure 12F:
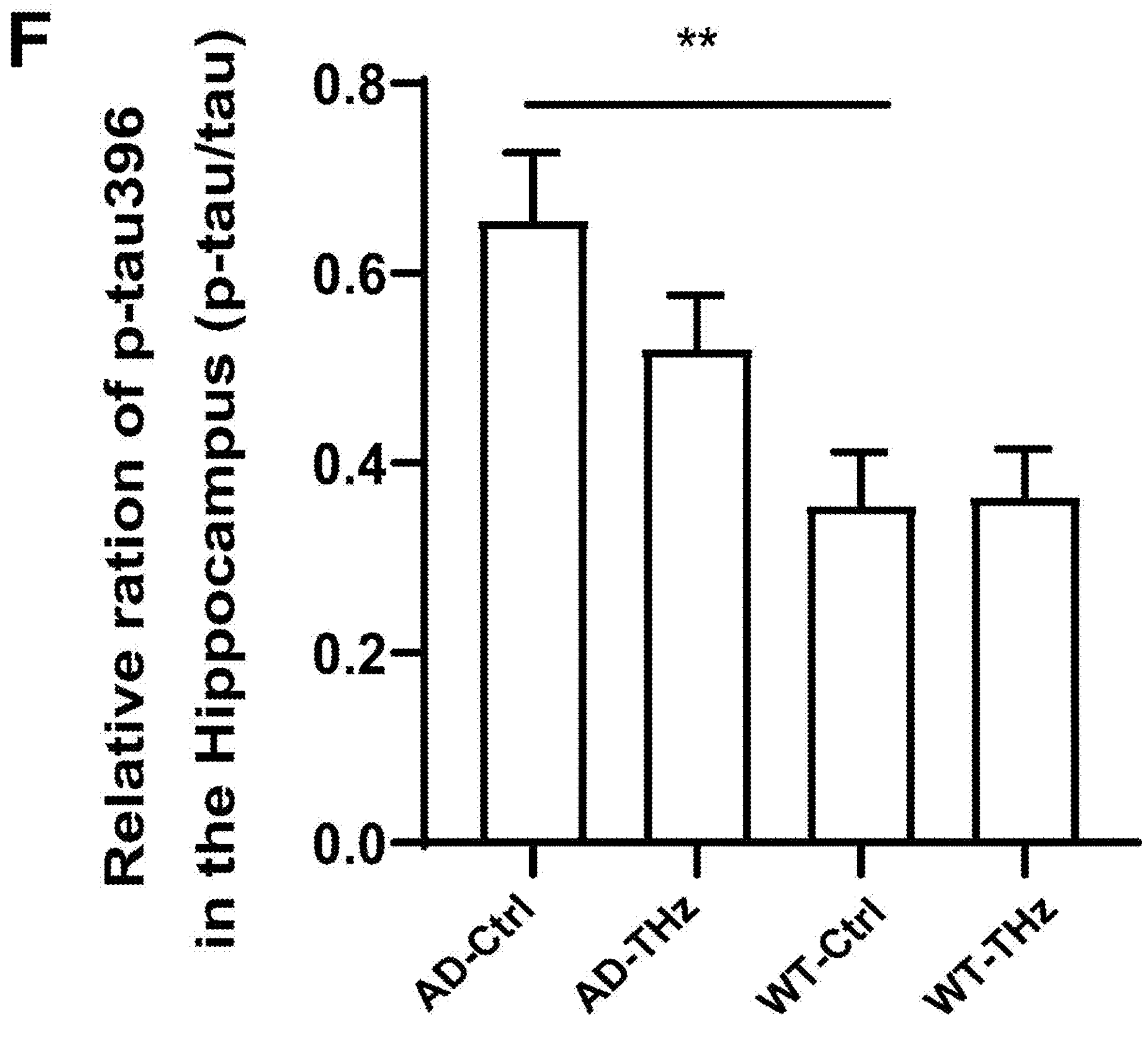

Western blot further confirmed that the higher levels of tau hyperphosphorylation in the AD mice in Example 3 than that of the WT mice in Example 4 in the cortex ($p<0.01$; FIG. 12E). Western blotting also showed that THz wave attenuated tau hyperphosphorylation ($p<0.01$; FIG. 12E) in the AD mice with THz irradiation in Example 1 vs the AD mice in Example 3 in the cortex. There were moderately reduced in the hippocampus of the AD mice with THz irradiation in Example 1 ($p>0.05$; FIG. 12F), compared with the AD mice in Example 3. These results indicate that THz treatment may shield the AD brains against tau hyperphosphorylation.

FIGS. 13A-13J are schematic diagrams of neuronal and dendritic changes in AD mice after THz irradiation provided by an embodiment of the present disclosure.

Neuronal degeneration is an event downstream of Aβ oligomer toxicity. To further examine the potential effect of THz treatment on neurons in the AD brain, we performed immunofluorescence staining using antibodies against NeuN, microtubule-associated protein 2 (MAP-2), and synaptophysin in the cortex and hippocampus of mice brain.

Figure 13A:
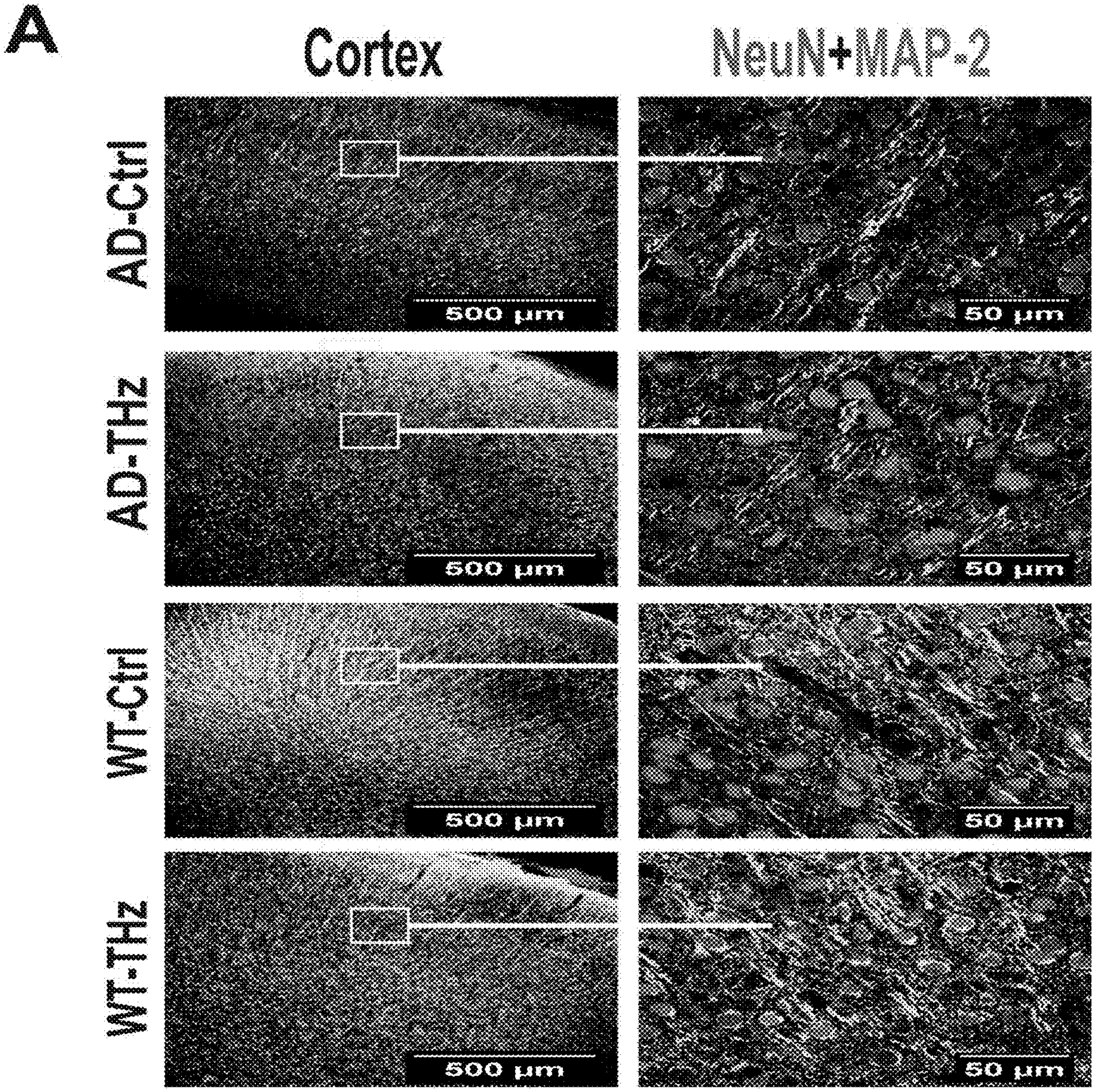
FIGS. 13A-13J are schematic diagrams of neuron changes in the brain of mice after THz irradiation provided by an embodiment of the present disclosure.
Figure 13B:
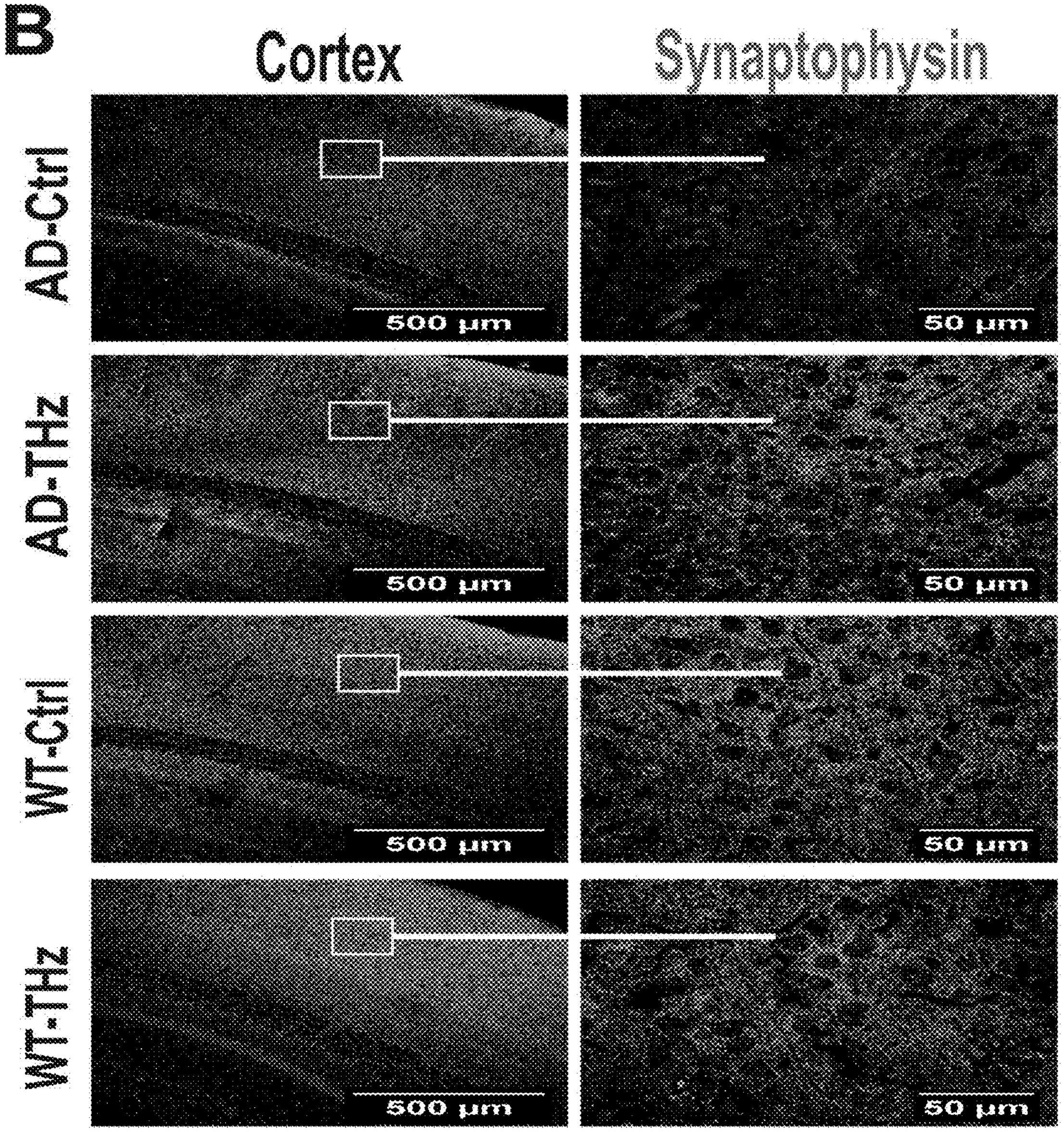
Figure 13C:
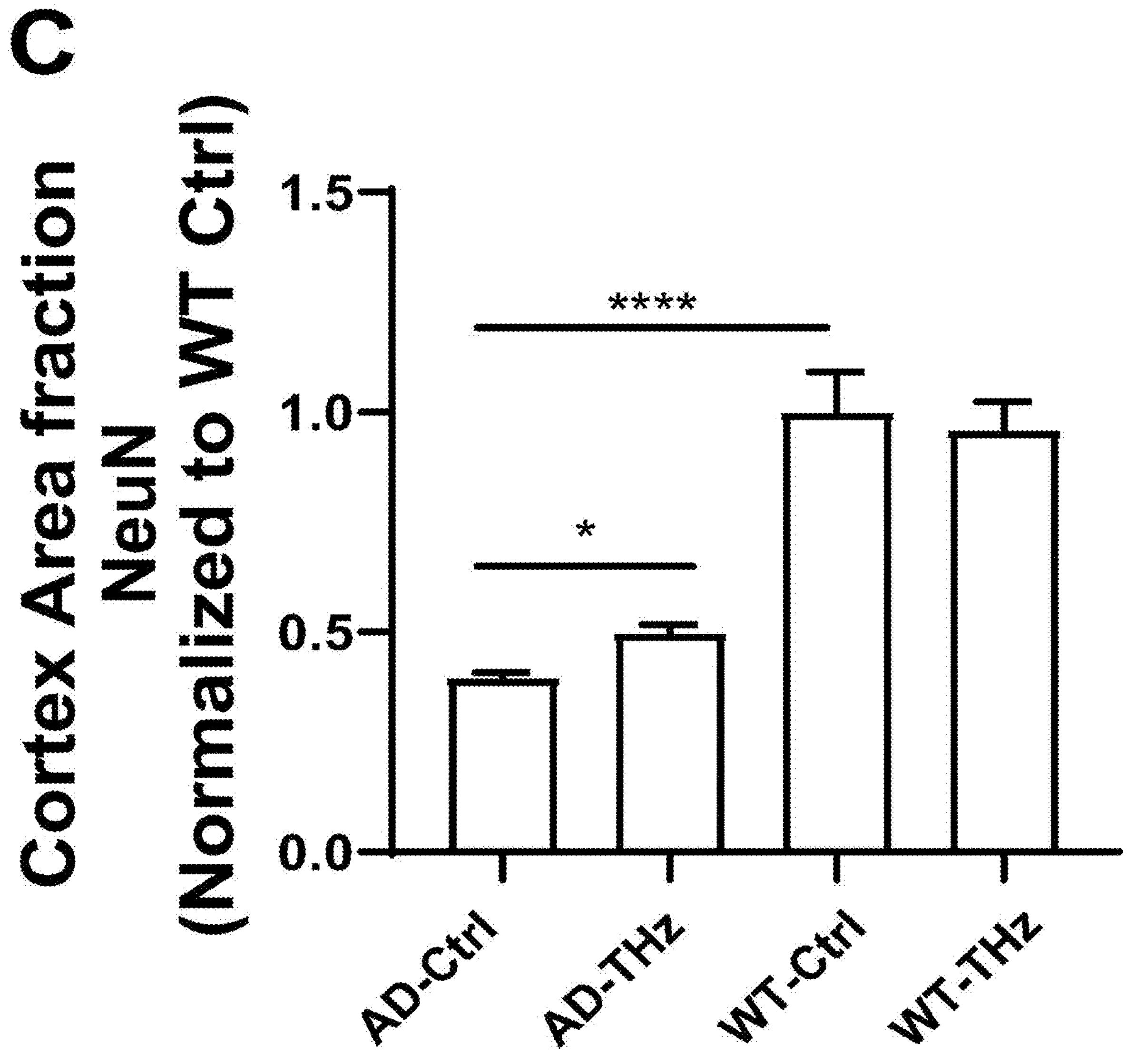
Figure 13D:
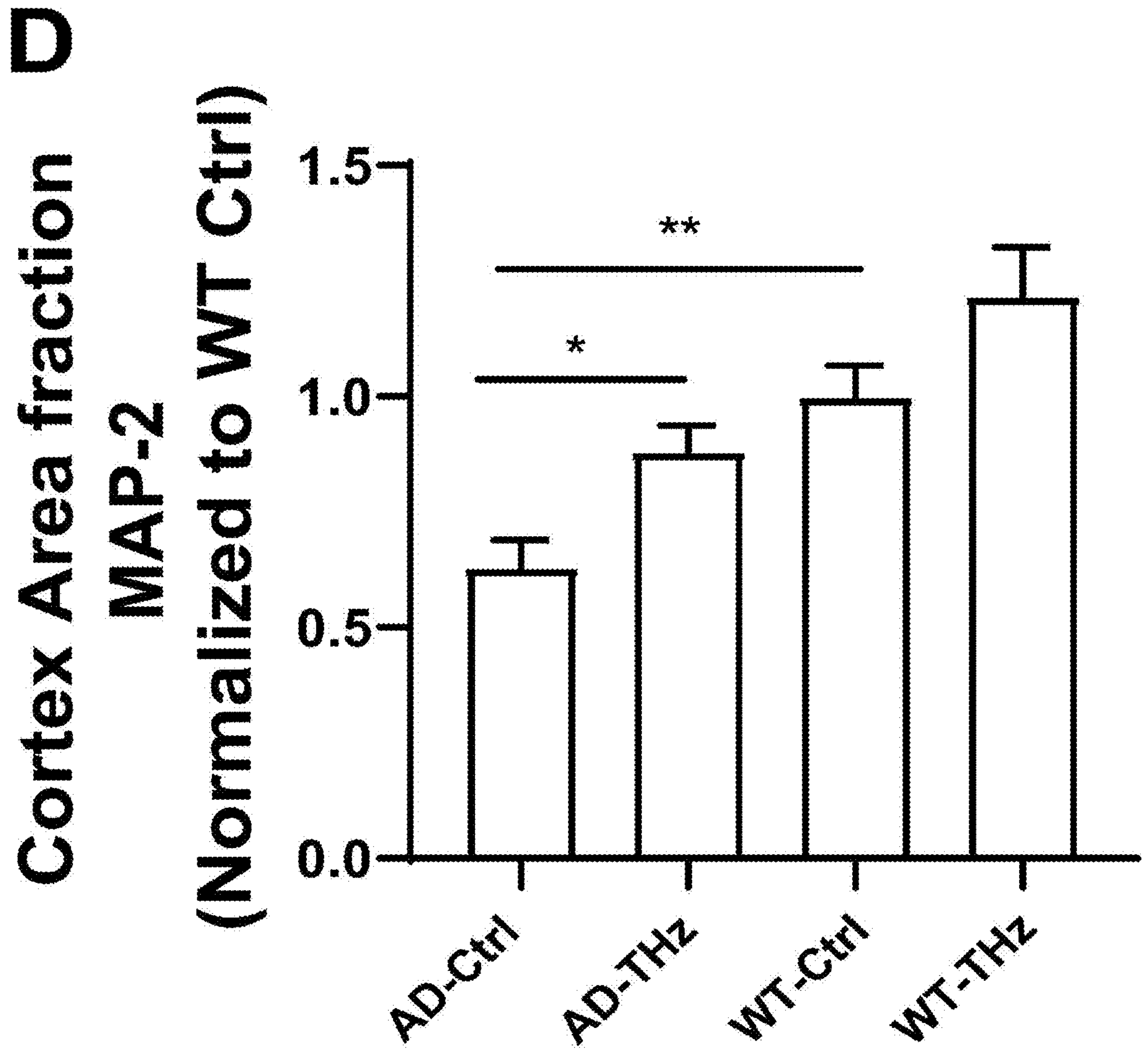
Figure 13E:
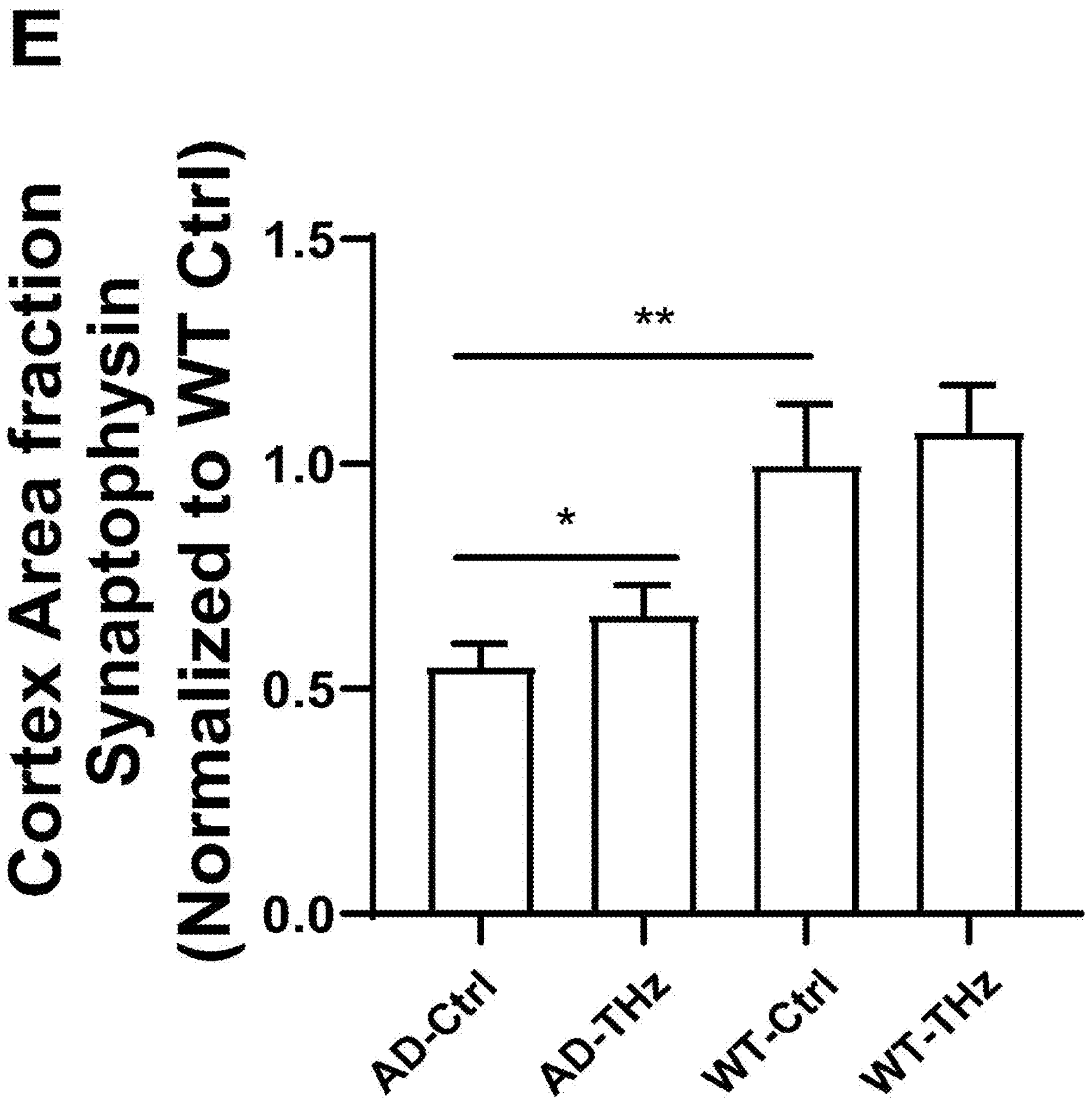
Figure 13F:
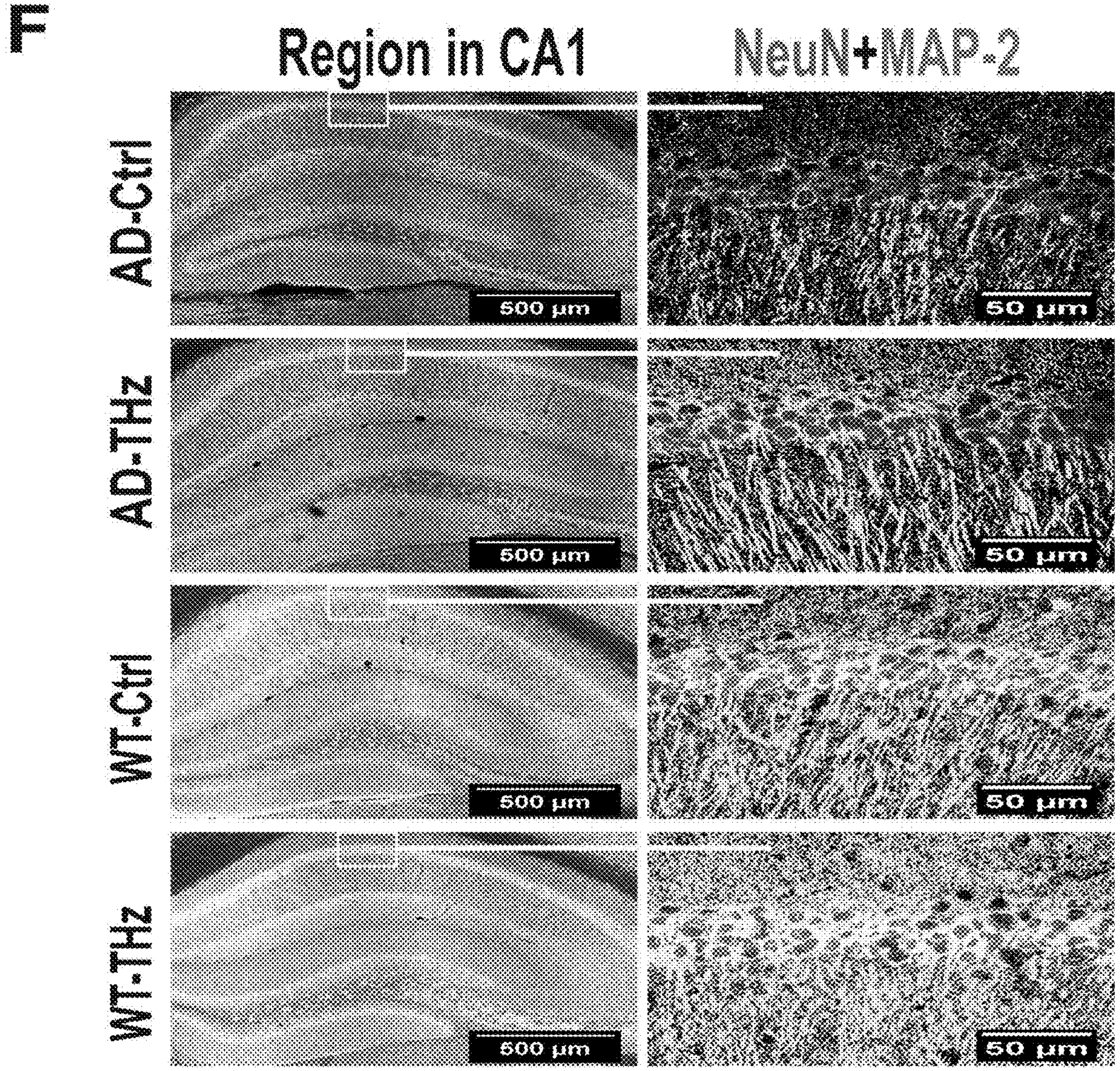
Figure 13G:
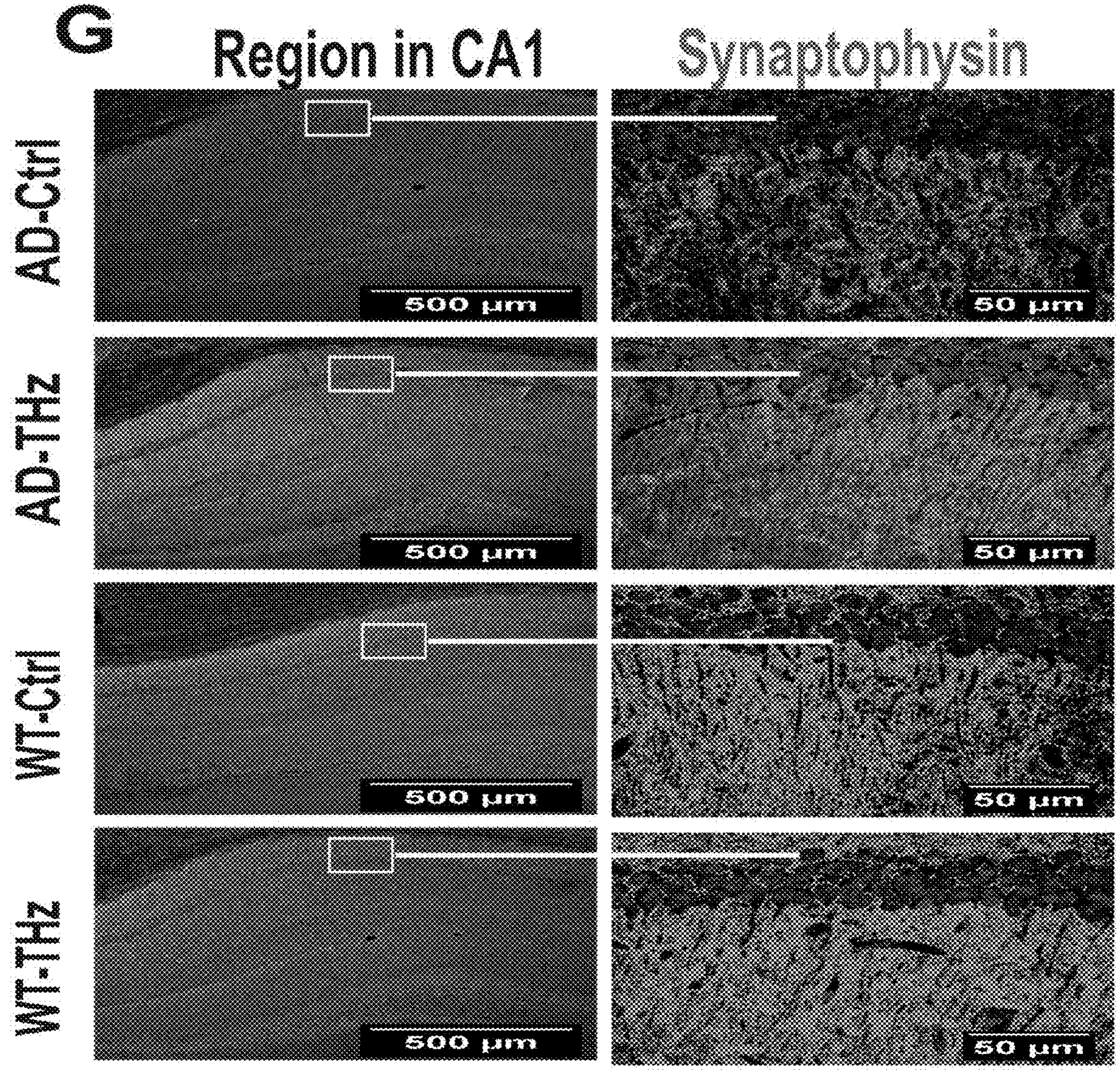

As shown in FIG. 13C, FIG. 13D, and FIG. 13E, we found that AD mice in Example 3 at 8 months old showed significant neuronal and dendritic loss in the cortex compared to the WT mice in Example 4 (respectively, $p<0.0001$, $p<0.01$, $p<0.01$; FIG. 13C, FIG. 13D, and FIG. 13E), whereas THz wave treatment remarkably reversed neuronal and dendritic loss, compared to AD mice in Example 3 in the AD mice with THz irradiation in Example 1, as shown by the changes of positive staining area fractions (respectively, all $p<0.05$; FIG. 13C, FIG. 13D, and FIG. 13E).

Figure 13H:
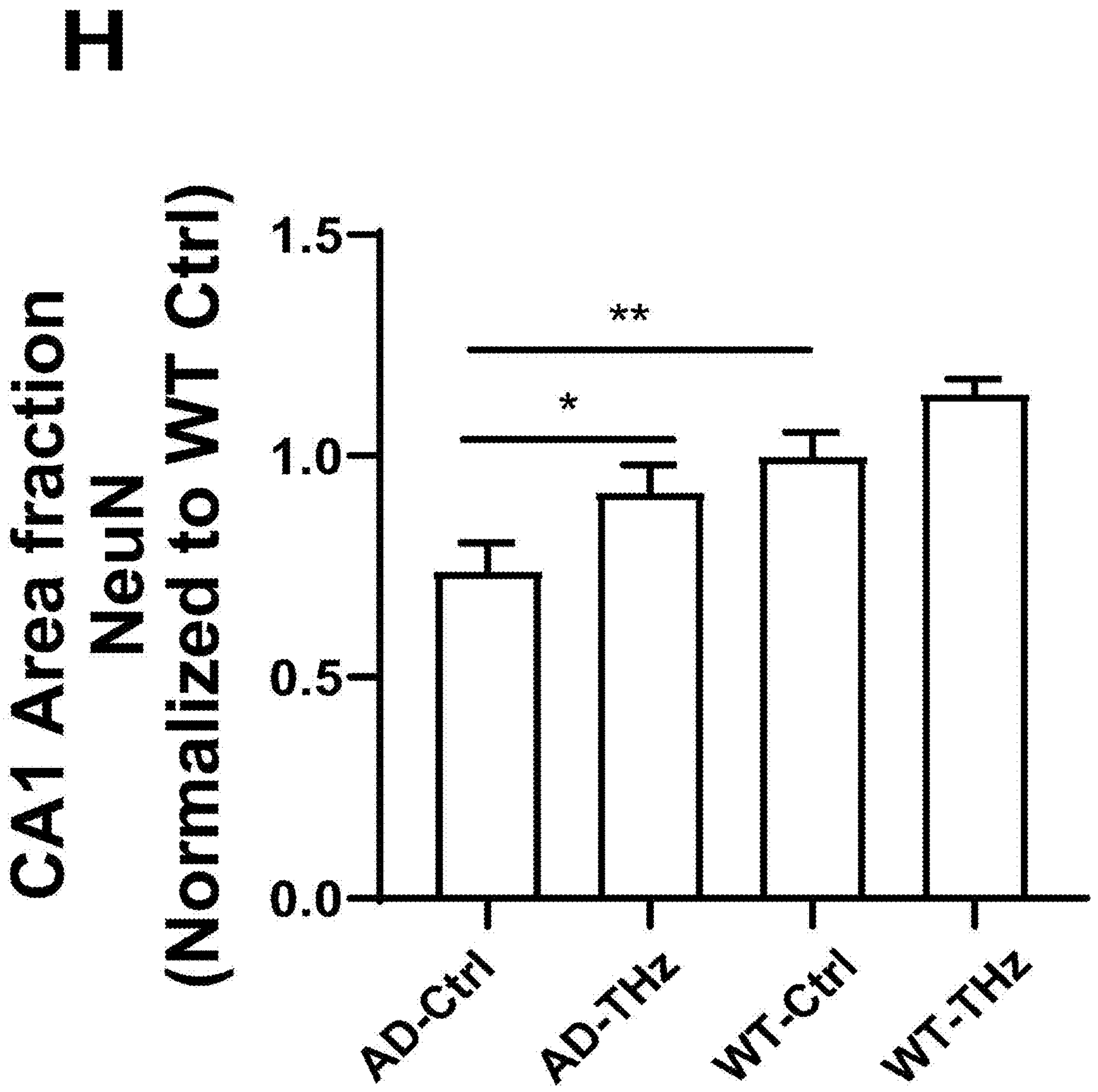
Figure 13I:
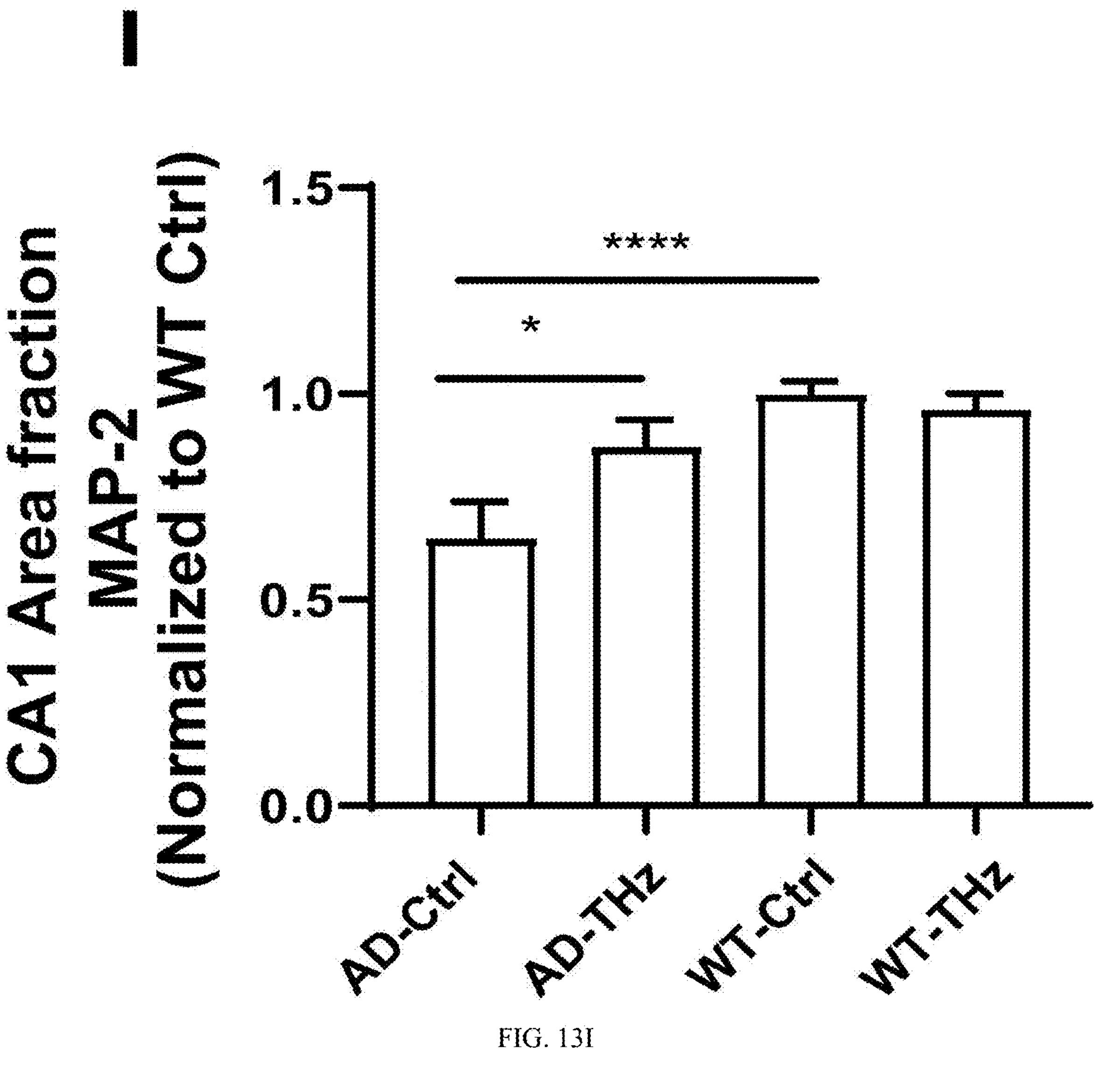
Figure 13J:
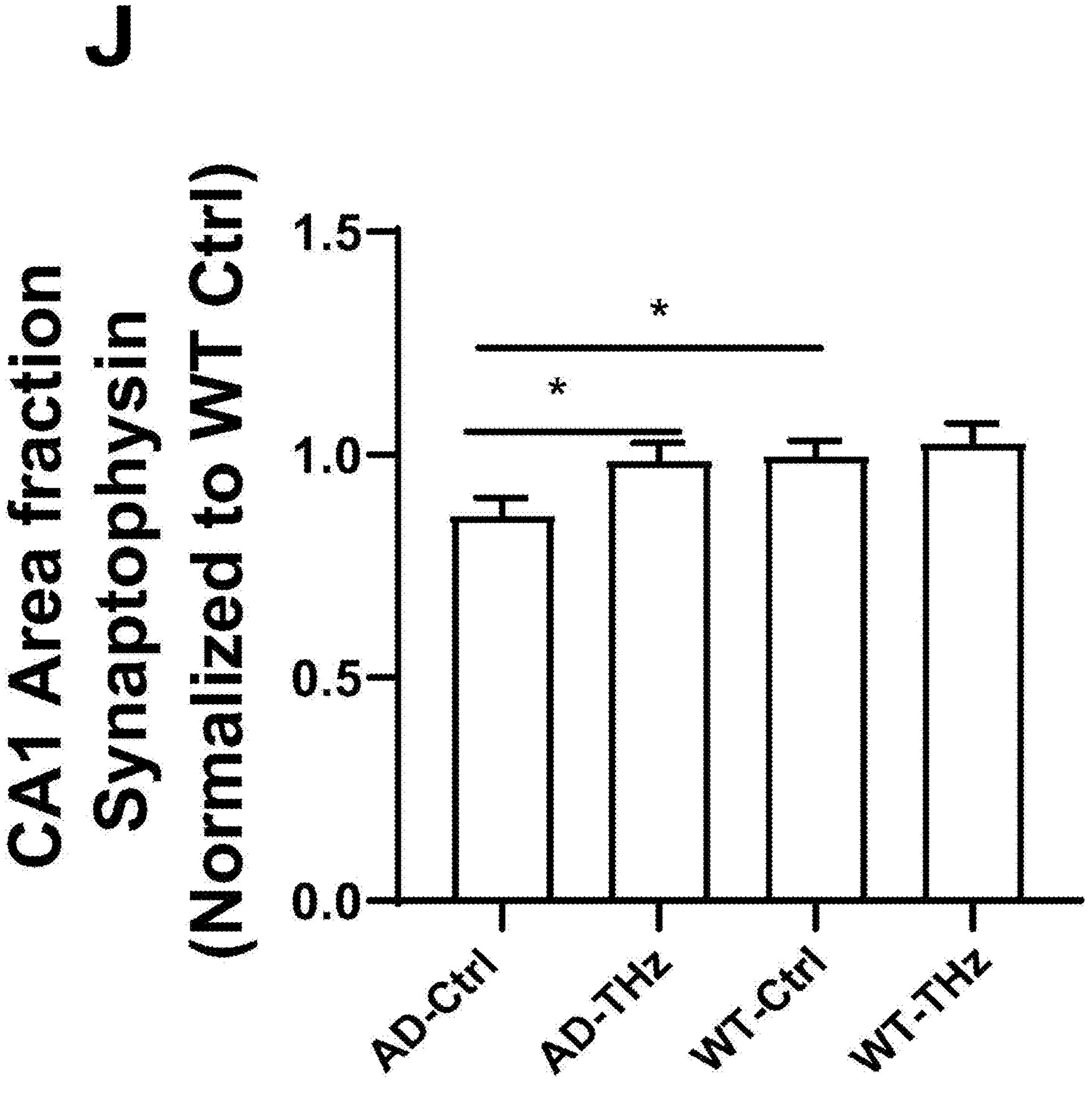

Further, we also found that AD mice in Example 3 at 8 months old showed significant neuronal and dendritic loss in the hippocampus compared to the WT mice in Example 4 (respectively, $p<0.01$, $p<0.0001$, $p<0.05$; FIG. 13H, FIG. 13I, and FIG. 13J), whereas THz wave treatment remarkably reversed neuronal and dendritic loss, compared to AD mice in Example 3 in the AD mice with THz irradiation in Example 1, as shown by the changes of positive staining area fractions (respectively, all $p<0.05$; FIG. 13H, FIG. 13I, and FIG. 13J). These results demonstrate that THz wave can ameliorate neuronal loss in the brain of AD mice.

To sum up, the symptoms of mice with AD were improved after the treatment of the method, system, and device for treating AD provided by the disclosure.

From the description of the above embodiments, those skilled in the art can clearly understand that each embodiment can be realized by employing software and necessary general hardware platforms, and of course, it can also be realized by hardware. Based on this understanding, the essence of the above technical solution or the part that has contributed to the prior art can be embodied in the form of a software product, which can be stored in a computer-readable storage medium, such as ROM/RAM, magnetic disk, optical disk, etc., and includes several instructions to make a computer device (which can be a personal computer, a server, or a network device, etc.) execute the methods of various embodiments or some parts of embodiments.

In this specification, specific examples are used to explain the principle and implementation of the present disclosure and the descriptions of the above examples are only used to help understand the method and core ideas of the present disclosure. At the same time, according to the idea of the present disclosure, there will be changes in the specific implementation and application scope for those ordinarily skilled in this field. To sum up, the content of this specification should not be construed as a limitation of the present disclosure.

REFERENCES

ADDIN EN.REFLIST 1. Niu, L., et al., Chronic sleep deprivation altered the expression of circadian clock genes and aggravated Alzheimer's disease neuropathology. Brain Pathol, 2022. 32(3): p. e13028.

2. Wang, Y., et al., The essential role of transcription factor Pitx3 in preventing mesodiencephalic dopaminergic neurodegeneration and maintaining neuronal subtype identities during aging. Cell Death Dis, 2021. 12(11): p. 1008.
3. Hardy, J. and D. J. Selkoe, The amyloid hypothesis of Alzheimer's disease: progress and problems on the road to therapeutics. Science, 2002. 297(5580): p. 353-6.
4. Blennow, K. and H. Zetterberg, Biomarkers for Alzheimer's disease: current status and prospects for the future. J Intern Med, 2018. 284(6): p. 643-63.

What is claimed is:

1. A test device for treating Alzheimer's disease (AD), comprising:

a terahertz (THz) wave generator, configured for generating a THz wave; wherein the THz wave has a pulse frequency of 0.14 THz and an irradiation power of 25 $mW/cm^2$; and a headgear, connected to the THz wave generator via an optical fiber, wherein the headgear is configured for precise irradiation of the THz wave to a specific brain region of an experimental animal.

2. The test device for treating the AD according to claim 1, further comprising:

a gas anesthesia machine and an anesthetic nasal mask, wherein the gas anesthesia machine is configured to continuously administer isoflurane to anesthetize the experimental animal, and the anesthetic nasal mask is positioned on a nose of the experimental animal for delivering of the isoflurane.

3. The test device for treating the AD according to claim 1, wherein the THz wave generator comprises a THz wave irradiation output, a direction indicator, a ventilation system, a power connector, an overheating LED, a modulation input, and a power switch.

4. The test device for treating the AD according to claim 1, wherein an inner side of the headgear is provided with an irradiation probe, and the irradiation probe comprises a THz irradiation probe.

5. The test device for treating the AD according to claim 4, wherein an outer side of the headgear is provided with a connecting hole, a position of the connecting hole corresponds to a position of the irradiation probe, and the headgear is connected to the THz wave generator through the connecting hole.

6. The test device for treating the AD according to claim 1, further comprising a pulse regulator; wherein the pulse regulator is connected to the THz wave generator via a coaxial transmission line, and the pulse regulator is configured for modulating a pulse intensity of the THz wave emitted by the THz wave generator.

7. The test device for treating the AD according to claim 1, further comprising a stereotaxic apparatus; wherein the stereotaxic apparatus is configured for fixing and adjusting a position of the experimental animal, ensuring an accurate irradiation of the specific brain region by the THz wave emitted from the THz wave generator.

8. A test method for treating AD, comprising:

anaesthetizing an experimental animal and fixing the experimental animal in a stereotaxic apparatus;

irradiating the experimental animal with a THz wave to obtain an irradiated experimental animal, wherein the THz wave has a pulse frequency of 0.14 THz and an irradiation power of 25mW/$cm^2$; and conducting behavioral and pathological tests on the irradiated experimental animal, and determining a treatment result.

9. A test system for treating AD, comprising:

an anesthesia module, configured to anaesthetize an experimental animal and fix the experimental animal in a stereotaxic apparatus;

an irradiation module, configured to irradiate the experimental animal with a THz wave, wherein the THz wave has a pulse frequency of 0.14 THz and an irradiation power of 25mW/$cm^2$; and a detection module, configured to conduct behavioral and pathological tests on an irradiated experimental animal, and determine a treatment result.

10. An electronic device, comprising a memory, a processor, and a computer program stored in the memory and executable on the processor, wherein when the processor executes the computer program, the test method for treating the AD according to claim 8 is realized;

the test method for treating the AD comprises:

anaesthetizing an experimental animal and fixing the experimental animal in a stereotaxic apparatus;

irradiating the experimental animal with a THz wave to obtain an irradiated experimental animal, wherein the THz wave has a pulse frequency of 0.14 THz and an irradiation power of 25mW/$cm^2$; and conducting behavioral and pathological tests on the irradiated experimental animal and determining a treatment result.

* * * * *